(12) United States Patent
Lalaoui et al.

(10) Patent No.: US 9,861,679 B2
(45) Date of Patent: Jan. 9, 2018

(54) METHOD OF TREATING CANCER

(71) Applicant: THE WALTER AND ELIZA HALL INSTITUTE OF MEDICAL RESEARCH, Victoria (AU)

(72) Inventors: Najoua Lalaoui, Victoria (AU); John Henry Silke, Victoria (AU); David Laurence Vaux, Victoria (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 0 days.

(21) Appl. No.: 14/875,537

(22) Filed: Oct. 5, 2015

(65) Prior Publication Data

US 2016/0184383 A1 Jun. 30, 2016

(30) Foreign Application Priority Data

Oct. 3, 2014 (WO) ................ PCT/AU2014/050266

(51) Int. Cl.
| | | |
|---|---|---|
| *A61K 38/00* | (2006.01) | |
| *C07K 9/00* | (2006.01) | |
| *A61K 38/05* | (2006.01) | |
| *A61K 38/04* | (2006.01) | |
| *C07K 5/062* | (2006.01) | |
| *A61K 38/19* | (2006.01) | |
| *A61K 31/7125* | (2006.01) | |
| *A61K 45/06* | (2006.01) | |

(52) U.S. Cl.
CPC ........... *A61K 38/05* (2013.01); *A61K 31/7125* (2013.01); *A61K 38/04* (2013.01); *A61K 38/191* (2013.01); *A61K 45/06* (2013.01); *C07K 5/06026* (2013.01)

(58) Field of Classification Search
None
See application file for complete search history.

(56) References Cited

U.S. PATENT DOCUMENTS 7,378,249 B2 * 5/2008 Andre ............... C12N 15/111
435/7.1
2012/0252737 A1 * 10/2012 Yaffee ............... C12N 15/1137
514/19.3

FOREIGN PATENT DOCUMENTS

WO WO2013/049350 A1 * 4/2013

OTHER PUBLICATIONS

LY2228820 Dimesylate, a selective inhibitor of p38 Mitogen-activated Protein Kinase, Reduces Angiogenic Endothelial Cord formation in Vitro and in Vivo, The Journal of Biological Chemistry, vol. 288, No. 9, pp. 6743-6753, Mar. 1, 2013.*

* cited by examiner

*Primary Examiner* — Jeanette Lieb
(74) *Attorney, Agent, or Firm* — Karl Bozicevic; Bozicevic, Field and Francis LLP

(57) ABSTRACT

The present invention provides a method of treating cancer in a subject wherein the method comprising administering to the subject an IAP antagonist and a p38 and/or a MK2 inhibitor.

35 Claims, 8 Drawing Sheets

A

B

METHOD OF TREATING CANCER

RELATED APPLICATIONS

This application is associated with and claims priority from International patent application no. PCT/AU2014/050266 filed on 3 Oct. 2014, the entire contents of which is incorporated herein by reference.

FIELD OF INVENTION

The present invention relates to a method of treating cancer. The method involves the administration of an Inhibitor of Apoptosis (IAP) antagonist in combination with a p38 or a MK2 inhibitor, or both a p38 inhibitor and a MK2 inhibitor.

BACKGROUND OF INVENTION

Inhibitor of Apoptosis (IAPs) proteins are endogenous inhibitors of programmed cell death. Elevated levels of IAPs are often found in cancers, due to gene amplification, translocation, or overexpression (Fulda and Vucic, 2012). In vitro and in vivo studies have associated high IAP levels with tumorigenesis, chemoresistance, disease progression, and poor prognosis (Hess et al., 2007; Nakagawa et al., 2006; Ramp et al., 2004; Tamm et al., 2004). The role of IAPs in regulating apoptosis, and the correlation of IAP expression with cancer progression provided the rationale for the design and development of IAP antagonist compounds (also known as "SMAC mimetics"), a new class of cancer therapeutic.

The key IAPs-XIAP, cIAP1 and cIAP2-bear three tandem Baculoviral IAP Repeat domains (BIRs) and a C-terminal E3 ligase RING domain. SMAC/Diablo is a natural IAP antagonist protein that when released from the mitochondria binds to IAPs (Du et al., 2000; Verhagen et al., 2000). SMAC mimetics are modeled on the N-terminal AVPI tetrapeptide of SMAC/Diablo and bind to the second and third BIR domain of IAPs. The development of SMAC mimetics has helped to define the exact role of IAPs in the regulation of cell death pathways. XIAP exhibits its anti-apoptotic activity through direct binding to and inhibition of caspase-3, -7 and -9 (Srinivasula et al., 2001). cIAP1 and cIAP2 on the other hand are not direct caspase inhibitors, but regulate caspase activation indirectly through their E3 ligase activity (Bertrand et al., 2008; Eckelman and Salvesen, 2006; Vince et al., 2007). In response to TNFα, cIAP1 and cIAP2 ubiquitylate RIPK1 to lessen its ability to activate FADD and caspase-8 (Bertrand et al., 2008; Feoktistova et al., 2011). Within the TNFα/TNFR1 complex cIAPs promote activation of p65/RelA NF-κB, whereas in the cytosol they constitutively ubiquitylate NIK to reduce signaling by p100/p52 NF-κB2 (Feltham et al., 2011; Zarnegar et al., 2008).

Consequently, SMAC mimetics trigger apoptotic cell death in cancer cells in two ways. Firstly, by binding to the BIRs of cIAP1 and cIAP2 they trigger a conformational change which allows the RING domains to dimerise, activating their E3 ligase activity, leading to cIAP1 and cIAP2 auto-ubiquitylation and subsequent proteasomal degradation (Dueber et al., 2011; Feltham et al., 2010). cIAP1 and 2 degradation induces the activation of p52 NF-κB2 leading to synthesis of TNFα. The autocrine secretion of TNFα activates TNFR1 signaling that, in the absence of cIAP1 and 2, results in the activation of caspase-8 (Feoktistova et al., 2011). Secondly, binding of SMAC mimetics to XIAP's BIR domains prevents XIAP from directly binding to and inhibiting caspases-3, -7 and -9.

In vitro and in vivo studies have demonstrated that SMAC mimetics have excellent anti-tumour activity as single agents in several cancer cell lines (Fulda and Vucic, 2012). Moreover when combined with some conventional chemotherapeutic agents, SMAC mimetics display synergistic effects (Fulda and Vucic, 2012) Importantly, administration of SMAC mimetics showed no significant toxicity in mouse xenograft models (Fulda and Vucic, 2012). Based on the positive results from preclinical studies, several SMAC mimetics have completed phase I safety studies in the clinic. Amongst them, the TetraLogic compound called Birinapant (TL32711) is the most advanced. A Phase I study in patients with advanced solid tumours and lymphoma showed that intravenous administration was well tolerated with no dose-limiting toxicities and demonstrated evidence of anti-tumour activity (Amaravadi et al Poster abstract #2532. 102nd AACR annual meeting. 2011, Orlando, Fla.). A Phase Ib/IIa five-arm study of Birinapant in combination with four different chemotherapies is currently under way (ClinicalTrial.gov, NCT01188499). Additional Phase I and II clinical studies are recruiting for both solid tumours and hematological malignancies (ClinicalTrial.gov, NCT01573780, NCT01486784).

The p38 pathway regulates key cellular signaling related to inflammation. For instance, upon Toll Like Receptor (TLR) activation, p38 induces a phosphorylation cascade involving kinases and transcription factors leading to TNFα transcription and secretion (Gaestel, 2013). The kinase MK2 has been demonstrated to be the downstream mediator of p38 that serves to activate TNFα transcription in response to TLRs (Gaestel, 2013). Its crucial role in inflammatory cytokine expression has been exploited to develop p38 inhibitors to inhibit TNFα production in auto-immune diseases. To date, several orally active p38 inhibitors have entered clinical trials (Cohen and Alessi, 2013). However, despite encouraging preclinical findings, none of these compounds advanced to late stage clinical trials due to lack of efficacy and/or unacceptable side effects (Cohen and Alessi, 2013). In recent years, several potential reasons have come to light to explain why p38 may not be an optimal target for the development of anti-inflammatory drugs. For example, p38 participates in feedback control loops that suppress the activities of 'upstream' MAPK, implicated in the activation of the MAPK JNKs, which stimulate the production of TNFα during inflammatory processes. Therefore, drugs that inhibit p38 cancel these feedback control loops, leading to a hyperactivation of JNKs and a consequent increase in pro-inflammatory cytokines that may contribute to the modest clinical responses and hepatic toxicities (Cohen and Alessi, 2013).

SUMMARY OF INVENTION

The present inventors have surprisingly found that a combination of an IAP antagonist with a p38 or MK2 inhibitor, or both, provides a highly efficacious treatment of cancer.

Accordingly, in a first aspect, the present invention provides a method of treating cancer in a subject, the method comprising administering to the subject an IAP antagonist in combination with a p38 or MK2 inhibitor, or with both a p38 inhibitor and a MK2 inhibitor.

In a second aspect the present invention provides the use of a combination of an IAP antagonist and a p38 or MK2 inhibitor, or both a p38 and MK2 inhibitor in the treatment of cancer in a subject.

In a third aspect the present invention provides the use of a combination of an IAP antagonist and a p38 or MK2 inhibitor, or both a p38 and MK2 inhibitor in the preparation of a medicament for the treatment of cancer in a subject.

In a fourth aspect the present invention provides a pharmaceutical preparation comprising an IAP antagonist and a p38 or a MK2 inhibitor, or both a p38 and MK2 inhibitor.

DETAILED DESCRIPTION OF THE INVENTION

Figure 1:
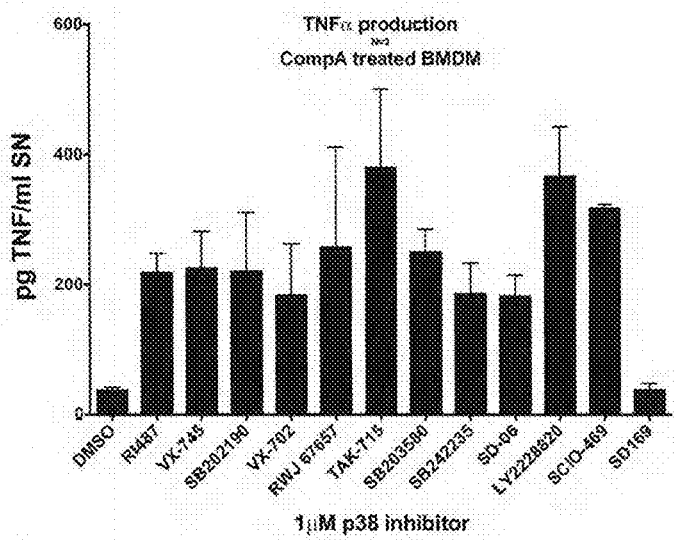
FIG. 1: p38 inhibitors increase TNFα production and cell death induced by SMAC mimetics. A. Bone Marrow Derived Macrophages (BMDM) were pretreated ±1 μM of the indicated p38 inhibitors for 30 min then treated with 500 nM of SMAC mimetic Compound A (CompA) for 24 h. TNFα production was measured by ELISA of supernatants. B. BMDM were pretreated 500 nM of SMAC mimetic Compound A, GT13072 or birinapant ±1 μM of LY2228820. TNFα production was measured by ELISA of supernatants. N=3 biological repeats and error bars are SEM. C. BMDM were pretreated±the indicated dose of MK2 inhibitor PF-3644022 and the p38 inhibitor LY2228820, VX-702, TAK-715 or VX-745 for 30 min then treated with 500 nM of SMAC mimetic Compound A. Cell viability was measured after 24 h of treatment using CellTiter-Glo® (CTG) reagent. N=3 biological repeats and error bars are SEM.
Figure 1:
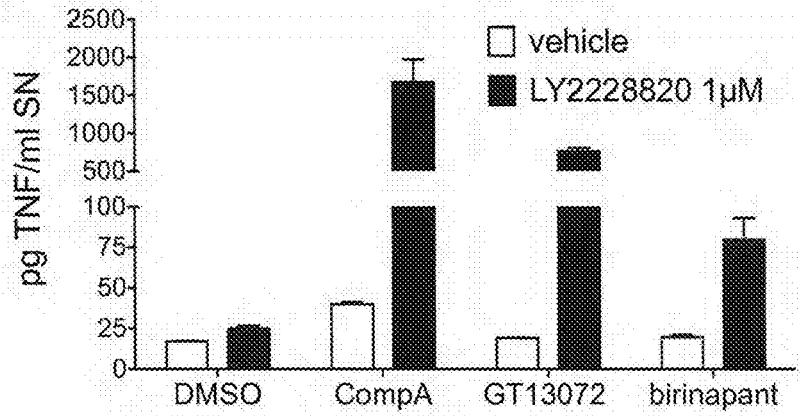
Figure 1:
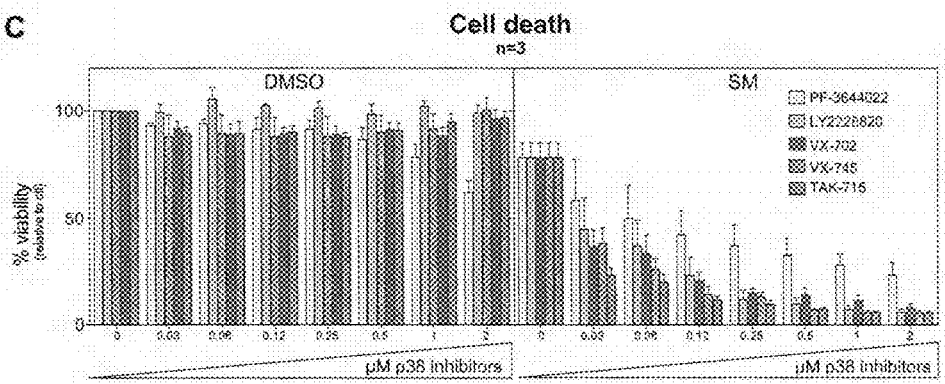

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "an agent" includes a single agent, as well as two or more agents; reference to "a molecule" includes a single molecule, as well as two or more molecules; and so forth.

Accordingly, in a first aspect, the present invention provides a method of treating a tumour in a subject, the method comprising administering to the subject an IAP antagonist in combination with a p38 or a MK2 inhibitor, or both a p38 inhibitor and a MK2 inhibitor.

The IAP family of proteins includes XIAP (BIRC4), cIAP1 (BIRC2), cIAP2 (BIRC3); NAIP (BIRC1), Survivin (BIRC5), Apollon (Bruce; BIRC6), ML-IAP (BIRC7; Livin, KIAP) and ILP2 (BIRC8). There is a degree of redundancy between family members, but genetic deletion of XIAP+ cIAP1+cIAP2 causes early embryonic lethality in mice. Molecules that efficiently target XIAP+cIAP1+cIAP2 promote inflammation and activate cell death signaling.

In an embodiment, the IAP is one or more of cIAP1, cIAP2 and XIAP.

cIAP1 is encoded by the sequence shown in GenBank DQ068066.1. Transcript variants of cIAP1 include NCBI reference sequences NM_001166.4, NM_001256163.1 and NM_001256166.1.

cIAP2 is encoded by the sequence shown in GenBank BC037420.1. Transcript variants of cIAP2 include NCBI reference sequences NM_001165.4 and NM_182962.2.

XIAP (X-linked inhibitor of apoptosis) is encoded by GenBank NCBI reference sequence NG_007264.1. Transcript variants of XIAP include NCBI reference sequences NM_001167.3, NM_001204401.1 and NR_037916.1.

Suitable IAP antagonists would be known to persons skilled in the art. Examples include the monovalent SMAC mimetics GDC-0145, GDC-0152, and GDC-0917 (Genentech, USA), AT-IAP (Astex, UK), and AT-406 (Ascenta, USA) and the bivalent SMAC mimetics AEG40826 (Aegera Therapeutics, USA), SM-1200 (Univ. of Michigan), HGS1029 (Human Genome Sciences, USA), BV6 (Genentech, USA), AEG40730 (Aegera Therapeutics); SM-164 (Univ. of Michigan); CS3 (Genentech); ML101 (Sanford-Burnham Medical Research Institute); AEG35156 (Aegera Therapeutics) and birinapant/TL32711 (TetraLogic, USA). Several of these are further discussed in Fulda and Vucic and Fulda and collaborators (Fulda, 2014; Fulda and Vucic, 2012), the contents of which are incorporated herein by reference. Whilst it is currently believed that both monovalent and bivalent SMAC mimetics can be used in the present invention it is presently preferred that the IAP antagonist is bivalent.

In an embodiment, the IAP antagonist is a mimetic of second mitochondria-derived activator of caspase (SMAC). SMAC is a pro-apoptotic mitochondrial protein that is an endogenous inhibitor of IAPs. SMAC mimetics have been shown to stimulate programmed cell death and thus have become a focus in the development of novel cancer therapeutics. SMAC mimetics comprise the IAP antagonists listed above.

SMAC antagonises IAP-mediated caspase inhibition by direct interaction with IAPs and/or induces proteasomal degradation of some members of the IAP family (cIAP1 and cIAP2). The ability of SMAC to promote both the proteolytic activation of pro-caspase-3 and the enzymatic activity of mature caspase-3 depends on its ability to specifically interact with IAP. SMAC binds to the BIR1/BIR2 linker region and BIR3 of XIAP disrupting the inhibition of caspase-3 and -7 and caspase-9 thus facilitating apoptosis or programmed cell death. SMAC and SMAC mimetics also induce proteasomal degradation of cIAP1 and cIAP2 resulting in the inhibition of canonical NF-κB activation. Many viruses modulate NF-κB activation to promote disease pathogenesis (Hiscott et al., 2006; Rahman and McFadden, 2011; Shukla et al., 2011).

The discovery of SMAC mimetics was enabled by the elucidation of the crystal structure of the interaction between SMAC and IAPs. SMAC mimetics appear to facilitate apoptotic cell death in tumour cells through multiple mechanisms, including binding directly to and antagonising IAPs, eliminating IAPs by promoting autoubiquitylation and proteasomal degradation of cIAPs and activation of a cell's extrinsic apoptotic pathway through TNFα stimulation.

Examples of SMAC peptidomimetics, including some of those identified above, are disclosed in, without limitation, U.S. Pat. No. 7,517,906; U.S. Pat. No. 7,419,975; U.S. Pat. No. 7,589,118; U.S. Pat. No. 7,932,382; U.S. Pat. No. 7,345,081; U.S. Pat. No. 7,244,851; U.S. Pat. No. 7,674,787; U.S. Pat. No. 7,772,177; U.S. Pat. No. 7,989,441; U.S. Pat. No. 8,716,236; US20100324083; US20100056467; US20090069294; US20110065726; US20110206690; WO2013127729; WO2014009495; WO2011098904; WO2013127729; WO2014090709; WO2014085489; WO2014031487; WO2013103703; WO2014055461; WO2014025759; WO2014011712. The compounds disclosed therein, and SMAC mimetics generally, have the structure:

$$[P1\text{-}P2\text{-}P3\text{-}P4] \qquad \text{(Formula I)}$$

or $$[P1\text{-}P2\text{-}P3\text{-}P4]\text{-}L\text{-}[P1'\text{-}P2'\text{-}P3'\text{-}P4'] \qquad \text{(Formula II)}$$

wherein P1-P2-P3- and P1'-P2'-P3'- correspond to peptide replacements, i.e., peptidomimetics, of the N-terminal Ala-Val-Pro-tripeptide of mature SMAC and P4 and P4' correspond to amino acid replacements of the fourth N-terminal amino acid, Phe, Tyr, He, or Val, and L is a linking group or bond covalently linking [P1-P2-P3-P4] to [P1'-P2'-P3'-P4'].

For example, without limitation, a SMAC mimetic may reside in the following genus of compounds of Formula II:

P1 and P1' are $NHR^1$—$CHR^2$—$C(O)$—;

P2 and P2' are —NH—$CHR^3$—$C(O)$—;

P3 and P3' are pyrrolidine, pyrrolidine fused to a cycloalkyl, or pyrrolidine fused to a heterocycloalkyl having a —N— heteroatom, optionally substituted in each case, and wherein the pyrrolidine of P3/P3' is bound to P2/P2' by an amide bond;

P4 and P4' are -M-$Q_p$-$R^7$.

The variable substituents can be, for example:

$R^1$: —H or —CH3;

$R^2$: —CH3, —CH2CH3 or —CH2OH;

$R^3$: C2-6 alkyl, C2-6 alkoxy, C3-C6 cycloalkyl or heterocycloalkyl, or C6-C8 aryl or heteroaryl, optionally substituted in each case;

M: a covalent bond, C1-6 alkylene, substituted C1-C6 alkylene such as but not limited to —C(O)—;

Q: a covalent bond, C1-6 alkylene, substituted C1-C6 alkylene, —O— or —$NR^8$—,

P: 0 or 1;

$R^7$: cycloalkyl, cycloalkylaryl, alkylaryl, alkylheteroaryl, aryl or heteroaryl, optionally substituted in each case;

$R^8$: —H or C1-6 alkyl.

L is a linking group or bond covalently linking [P1-P2-P3-P4] to [P1'-P2'-P3'-P4'].

"Alkyl" (monovalent) and "alkylene" (divalent) when alone or as part of another term (e.g., alkoxy) mean branched or unbranched, saturated aliphatic hydrocarbon group, having up to 12 carbon atoms unless otherwise specified. Examples of particular alkyl groups include, but are not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The term, "lower," when used to modify alkyl, alkenyl, etc., means 1 to 4 carbon atoms, branched or linear so that, e.g., the terms "lower alkyl", "$C_1$-$C_4$ alkyl" and "alkyl of 1 to 4 carbon atoms" are synonymous and used interchangeably to mean methyl, ethyl, 1-propyl, isopropyl, 1-butyl, sec-butyl or t-butyl. Examples of alkylene groups include, but are not limited to, methylene, ethylene, n-propylene, n-butylene and 2-methyl-butylene.

The term substituted alkyl refers to alkyl moieties having substituents replacing one or more hydrogens on one or more (often no more than four) carbon atoms of the hydrocarbon backbone. Such substituents are independently selected from the group consisting of: a halogen (e.g., I, Br, Cl, or F, particularly fluoro(F)), hydroxy, amino, cyano, mercapto, alkoxy (such as a $C_1$-$C_6$ alkoxy, or a lower ($C_1$-$C_4$) alkoxy, e.g., methoxy or ethoxy to yield an alkoxyalkyl), aryloxy (such as phenoxy to yield an aryloxyalkyl), nitro, oxo (e.g., to form a carbonyl), carboxyl (which is actually the combination of an oxo and hydroxy substituent on a single carbon atom), carbamoyl (an aminocarbonyl such as $NR_2C(O)$—, which is the substitution of an oxo and an amino on a single carbon atom), cycloalkyl (e.g., a cycloalkylalkyl), aryl (resulting for example in aralkyls such as benzyl or phenylethyl), heterocyclylalkyl (e.g., heterocycloalkylalkyl), heteroaryl (e.g., heteroarylalkyl), alkylsulfonyl (including lower alkylsulfonyl such as methylsulfonyl), arylsulfonyl (such as phenylsulfonyl), and —$OCF_3$ (which is a halogen substituted alkoxy). The invention further contemplates that several of these alkyl substituents, including specifically alkoxy, cycloalkyl, aryl, heterocyclyalkyl and heteroaryl, are optionally further substituted as defined in connection with each of their respective definitions provided below. In addition, certain alkyl substituent moieties result from a combination of such substitutions on a single carbon atom. For example, an ester moiety, e.g., an alkoxycarbonyl such as methoxycarbonyl, or tert-butoxycarbonyl (Boc) results from such substitution. In particular, methoxycarbonyl and Boc are substituted alkyls that result from the substitution on a methyl group (—$CH_3$) of both an oxo (═O) and an unsubstituted alkoxy, e.g., a methoxy ($CH_3$—O) or a tert-butoxy (($CH_3$)$_3$C—O—), respectively replacing the three hydrogens. Similarly, an amide moiety, e.g., an alkylaminocarbonyl, such as dimethlyaminocarbonyl or methylaminocarbonyl, is a substituted alkyl that results from the substitution on a methyl group (—$CH_3$) of both an oxo (═O) and a mono-unsubstitutedalkylamino or, diunsubstitutedalkylamino, e.g., dimethylamino (—N—($CH_3$)$_2$), or methylamino (—NH—($CH_3$)) replacing the three hydrogens (similarly an arylaminocarbonyl such as diphenylaminocarbonyl is a substituted alkyl that results from the substitution on a methyl group (—$CH_3$) of both an oxo (═O) and a mono-unsubstitutedaryl(phenyl)amino). Exemplary substituted alkyl groups further include cyanomethyl, nitromethyl, hydroxyalkyls such as hydroxymethyl, trityloxymethyl, propionyloxymethyl, aminoalkyls such as aminomethyl, carboxylalkyls such as carboxymethyl, carboxyethyl, carboxypropyl, 2,3-dichloropentyl, 3-hydroxy-5-carboxyhexyl, acetyl (e.g., an alkanoyl, where in the case of acetyl the two hydrogen atoms on the —$CH_2$ portion of an ethyl group are replaced by an oxo (═O)), 2-aminopropyl, pentachlorobutyl, trifluoromethyl, methoxyethyl, 3-hydroxypentyl, 4-chlorobutyl, 1,2-dimethyl-propyl, pentafluoroethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino (iso-propyl), cycloalkylcarbonyl (e.g., cuclopropylcarbonyl) and 2-carbamoyloxyethyl. Particular substituted alkyls are substituted methyl groups. Examples of substituted methyl group include groups such as hydroxymethyl, protected hydroxymethyl (e.g., tetrahydropyranyl-oxymethyl), acetoxymethyl, carbamoyloxymethyl, trifluoromethyl, chloromethyl, carboxymethyl, carboxyl (where the three hydrogen atoms on the methyl are replaced, two of the hydrogens are replaced by an oxo (═O) and the other hydrogen is replaced by a hydroxy (—OH)), tert-butoxycarbonyl (where the three hydrogen atoms on the methyl are replaced, two of the hydrogens are replaced by an oxo (═O) and the other hydrogen is replaced by a tert-butoxy (—O—C(($CH_3$)$_3$), bromomethyl and iodomethyl. When the specification and especially the claims refer to a particular substituent for an alkyl, that substituent can potentially occupy one or more of the substitutable positions on the alkyl. For example, reciting that an alkyl has a fluoro substituent, would embrace mono-, di-, and possibly a higher degree of substitution on the alkyl moiety.

The term substituted alkylene refers to alkylene moieties having substituents replacing one or more hydrogens on one or more (often no more than four) carbon atoms of the hydrocarbon backbone where the alkylene is similarly substituted with groups as set forth above for alkyl.

Alkoxy is —O-alkyl. A substituted alkoxy is —O-substituted alkyl, where the alkoxy is similarly substituted with groups as set forth above for alkyl. One substituted alkoxy is acetoxy where two of the hydrogens in ethoxy (e.g., —O—$CH_2$—$CH_3$) are replaced by an oxo, (═O) to yield —O—C(O)—$CH_3$; another is an aralkoxy where one of the hydrogens in the alkoxy is replaced by an aryl, such as benzyloxy, and another is a carbamate where two of the hydrogens on methoxy (e.g., —O—$CH_3$) are replaced by oxo (═O) and the other hydrogen is replaced by an amino (e.g., —$NH_2$, —NHR or —NRR) to yield, for example, —O—C(O)—$NH_2$. A lower alkoxy is —O-lower alkyl.

"Alkenyl" (monovalent) and "alkenylene" (divalent) when alone or as part of another term mean an unsaturated hydrocarbon group containing at least one carbon-carbon double bond, typically 1 or 2 carbon-carbon double bonds, which may be linear or branched and which have at least 2 and up to 12 carbon atoms unless otherwise specified. Representative alkenyl groups include, by way of example, vinyl, allyl, isopropenyl, but-2-enyl, n-pent-2-enyl, and n-hex-2-enyl.

The terms substituted alkenyl and substituted alkenylene refer to alkenyl and alkenylene moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, oxo, carbamoyl, cycloalkyl, aryl, heterocyclyl, heteroaryl, alkylsulfonyl, arylsulfonyl and —$OCF_3$.

"Alkynyl" means a monovalent unsaturated hydrocarbon group containing at least one carbon-carbon triple bond, typically 1 carbon-carbon triple bond, which may be linear or branched and which have at least 2 and up to 12 carbon atoms unless otherwise specified. Representative alkynyl groups include, by way of example, ethynyl, propargyl, and but-2-ynyl.

"Cycloalkyl" when alone or as part of another term means a saturated or partially unsaturated cyclic aliphatic hydrocarbon group (carbocycle group), having 3 to 8 carbon atoms unless otherwise specified, such as cyclopropyl, cyclobutyl, cyclopentyl and cyclohexyl, and further includes polycyclic, including fused cycloalkyls such as 1,2,3,4-tetrahydonaphthalenyls (1,2,3,4-tetrahydonaphthalen-1-yl, and 1,2,3,4-tetrahydonaphthalen-2-yl), indanyls (indan-1yl, and indan-2-yl), isoindenyls (isoinden-1-yl, isoinden-2-yl, and isoinden-3-yl) and indenyls (inden-1-yl, inden-2-yl and inden-3-yl). A lower cycloalkyl has from 3 to 6 carbon atoms and includes cyclopropyl, cyclobutyl, cyclopentyl and cyclohexyl.

The term substituted cycloalkyl refers to cycloalkyl moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, mercapto, carboxyl, oxo, carbamoyl, alkyl, substituted alkyls such as trifluoromethyl, aryl, substituted aryls, heterocyclyl, heteroaryl, alkylsulfonyl, arylsulfonyl and —$OCF_3$. When the specification and especially the claims refer to a particular substituent for a cycloalkyl, that substituent can potentially occupy one or more of the substitutable positions on the cycloalkyl. For example, reciting that a cycloalkyl has a fluoro substituent, would embrace mono-, di-, and a higher degree of substitution on the cycloalkyl moiety. Examples of cycloalkyls include cyclopropy, cyclobutyl, cyclopentyl, cyclohexyl, tetrahydronaphthyl and indanyl.

"Aryl" when used alone or as part of another term means an aromatic carbocyclic group whether or not fused having the number of carbon atoms designated, or if no number is designated, from 6 up to 14 carbon atoms. Particular aryl groups include phenyl, naphthyl, biphenyl, phenanthrenyl, naphthacenyl, indolyl, and the like (see e.g., Lang's Handbook of Chemistry (Dean, J. A., ed) $13^{th}$ ed. Table 7-2 [1985]).

The term substituted aryl refers to aryl moieties having substituents replacing one or more hydrogens on one or more (usually no more than six) carbon atoms of the aromatic hydrocarbon core. Such substituents are independently selected from the group consisting of: halo (e.g., I, Br, Cl, F), hydroxy, amino, cyano, alkoxy (such as $C_1$-$C_6$ alkoxy and particularly lower alkoxy), substituted alkoxy, aryloxy (such as phenoxy), nitro, mercapto, carboxyl, carbamoyl, alkyl, substituted alkyl (such as trifluoromethyl), aryl, —$OCF_3$, alkylsulfonyl (including lower alkylsulfonyl), arylsulfonyl, heterocyclyl and heteroaryl. Examples of such substituted phenyls include but are not limited to a mono- or di (halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl; 3-fluorophenyl, 4-fluorophenyl, a mono- or di (hydroxy) phenyl group such as 4-hydroxyphenyl, 3-hydroxyphenyl, 2,4-dihydroxyphenyl, the protected-hydroxy derivatives thereof; a nitrophenyl group such as 3- or 4-nitrophenyl; a cyanophenyl group, for example, 4-cyanophenyl; a mono- or di (lower alkyl) phenyl group such as 4-methylphenyl, 2,4-dimethylphenyl, 2-methylphenyl, 4-(iso-propyl) phenyl, 4-ethylphenyl, 3-(n-propyl) phenyl; a mono or di (alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(iso-propoxy)phenyl, 4-(t-butoxy)phenyl, 3-ethoxy-4-methoxyphenyl; 3- or 4-trifluoromethylphenyl; a mono- or dicarboxyphenyl or (protected carboxy) phenyl group such 4-carboxyphenyl; a mono- or di (hydroxymethyl) phenyl or (protected hydroxymethyl) phenyl such as 3-(protected hydroxymethyl) phenyl or 3,4-di (hydroxymethyl) phenyl; a mono- or di (aminomethyl) phenyl or (protected aminomethyl) phenyl such as 2-(aminomethyl) phenyl or 2,4-(protected aminomethyl) phenyl; or a mono- or di (N-(methylsulfonylamino)) phenyl such as 3-(N-methylsulfonylamino) phenyl. Also, the substituents, such as in a disubstituted phenyl groups, can be the same or different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, as well as for tri-substituted phenyl groups where the substituents are different, as for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. When the specification and especially the claims refer to a particular substituent for an aryl, that substituent can potentially occupy one or more of the substitutable positions on the aryl. For example, reciting that an aryl has a fluoro substituent, would embrace mono-, di-, tri, tetra and a higher degree of substitution on the aryl moiety. Fused aryl rings may also be substituted with the substituents specified herein, for example with 1, 2 or 3 substituents, in the same manner as substituted alkyl groups. The terms aryl and substituted aryl do not include moieties in which an aromatic ring is fused to a saturated or partially unsaturated aliphatic ring.

"Heterocyclic group", "heterocyclic", "heterocycle", "heterocyclyl", "heterocycloalkyl" or "heterocyclo" alone and when used as a moiety in a complex group, are used interchangeably and refer to any mono-, bi-, or tricyclic, saturated or unsaturated, non-aromatic hetero-atom-containing ring system having the number of atoms designated, or if no number is specifically designated then from 5 to about 14 atoms, where the ring atoms are carbon and at least one heteroatom and usually not more than four heteroatoms (i.e., nitrogen, sulfur or oxygen). Included in the definition are any bicyclic groups where any of the above heterocyclic rings are fused to an aromatic ring (i.e., an aryl (e.g., benzene) or a heteroaryl ring). In a particular embodiment the group incorporates 1 to 4 heteroatoms. Typically, a 5-membered ring has 0 to 1 double bonds and a 6- or 7-membered ring has 0 to 2 double bonds and the nitrogen or sulfur heteroatoms may optionally be oxidized (e.g., SO, $SO_2$), and any nitrogen heteroatom may optionally be quaternized. Particular unsubstituted non-aromatic heterocycles include morpholinyl (morpholino), pyrrolidinyls, oxiranyl, indolinyls, 2,3-dihydoindolyl, isoindolinyls, 2,3-dihydo-isoindolyl, tetrahydroquinolinyls, tetrahydroisoquinolinyls, oxetanyl, tetrahydrofuranyls, 2,3-dihydrofuranyl, 2H-pyranyls, tetrahydropyranyls, aziridinyls, azetidinyls, 1-methyl-2-pyrrolyl, piperazinyls and piperidinyls.

The term substituted heterocyclo refers to heterocyclo moieties having substituents replacing one or more hydrogens on one or more (usually no more than six) atoms of the heterocyclo backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, carboxyl, oxo, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituent for a heterocycloalkyl, that substituent can potentially occupy one or more of the substitutable positions on the heterocycloalkyl. For example, reciting that a heterocycloalkyl has a fluoro substituent, would embrace mono-, di-, tri, tetra and a higher degree of substitution on the heterocycloalkyl moiety.

"Heteroaryl" alone and when used as a moiety in a complex group refers to any mono-, bi-, or tricyclic aromatic ring system having the number of atoms designated, or if no number is specifically designated then at least one ring is a 5-, 6- or 7-membered ring and the total number of atoms is from 5 to about 14 and containing from one to four heteroatoms selected from the group consisting of nitrogen, oxygen, and sulfur (Lang's Handbook of Chemistry, supra). Included in the definition are any bicyclic groups where any of the above heteroaryl rings are fused to a benzene ring. The following ring systems are examples of the heteroaryl groups denoted by the term "heteroaryl": thienyls (alternatively called thiophenyl), furyls, imidazolyls, pyrazolyls, thiazolyls, isothiazolyls, oxazolyls, isoxazolyls, triazolyls, thiadiazolyls, oxadiazolyls, tetrazolyls, thiatriazolyls, oxatriazolyls, pyridyls, pyrimidinyls (e.g., pyrimidin-2-yl), pyrazinyls, pyridazinyls, thiazinyls, oxazinyls, triazinyls, thiadiazinyls, oxadiazinyls, dithiazinyls, dioxazinyls, oxathiazinyls, tetrazinyls, thiatriazinyls, oxatriazinyls, dithiadiazinyls, imidazolinyls, dihydropyrimidyls, tetrahydropyrimidyls, tetrazolo [1, 5-b] pyridazinyl and purinyls, as well as benzo-fused derivatives, for example benzoxazolyls, benzofuryls, benzothienyls, benzothiazolyls, benzothiadiazolyl, benzotriazolyls, benzoimidazolyls, isoindolyls, indazolyls, indolizinyls, indolyls, naphthyridines, pyridopyrimidines, phthalazinyls, quinolyls, isoquinolyls and quinazolinyls.

The term substituted heteroaryl refers to heteroaryl moieties (such as those identified above) having substituents replacing one or more hydrogens on one or more (usually no more than six) atoms of the heteroaryl backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituent for a heteroaryl, that substituent can potentially occupy one or more of the substitutable positions on the heteroaryl. For example, reciting that a heteroaryl has a fluoro substituent, would embrace mono-, di-, tri, tetra and a higher degree of substitution on the heteroaryl moiety.

Particular "heteroaryls" (including "substituted heteroaryls") include; 1H-pyrrolo[2,3-b]pyridine, 1, 3-thiazol-2-yl, 4-(carboxymethyl)-5-methyl-1, 3-thiazol-2-yl, 1,2,4-thiadiazol-5-yl, 3-methyl-1, 2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 1, 3-oxazol-2-yl, 1, 3,4-oxadiazol-5-yl, 2-methyl-1, 3,4-oxadiazol-5-yl, 2-(hydroxymethyl)-1, 3,4-oxadiazol-5-yl, 1, 2,4-oxadiazol-5-yl, 1, 3,4-thiadiazol-5-yl, 2-thiol-1, 3,4-thiadiazol-5-yl, 2-(methylthio)-1, 3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(methylsulfonic acid)-1H-tetrazol-5-yl, 2-methyl-1H-tetrazol-5-yl, 1, 2,3-triazol-5-yl, 1-methyl-1, 2,3-triazol-5-yl, 2-methyl-1, 2,3-triazol-5-yl, 4-methyl-1, 2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2, 6-dimethyl-as-triazin-3-yl, tetrazolo [1, 5-b] pyridazin-6-yl, 8-aminotetrazolo [1, 5-b]-pyridazin-6-yl, quinol-2-yl, quinol-3-yl, quinol-4-yl, quinol-5-yl, quinol-6-yl, quinol-8-yl, 2-methyl-quinol-4-yl, 6-fluoro-quinol-4-yl, 2-methyl, 8-fluoro-quinol-4-yl, isoquinol-5-yl, isoquinol-8-yl, isoquinol-1-yl, and quinazolin-4-yl. An alternative group of "heteroaryl" includes: 5-methyl-2-phenyl-2H-pyrazol-3-yl, 4-(carboxymethyl)-5-methyl-1, 3-thiazol-2-yl, 1, 3,4-triazol-5-yl, 2-methyl-1, 3,4-triazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tetrazolo [1, 5-b] pyridazin-6-yl, and 8-aminotetrazolo [1, 5-b] pyridazin-6-yl.

L is a linking group or a bond covalently linking one monomer, [P1-P2-P3-P4] to the other monomer, [P1'-P2'-P3'-P4']. Commonly, -L- links P2 to P2' position such as at R3 or P4 to P4' such as at M, G, Q, or $R^7$, or both P2 to P2' and P4 to P4'. L, therefore, can be a single or double covalent bond or a contiguous chain, branched or unbranched, substituted or unsubstituted, of 1 to about 100 atoms, typically 1 to about 30 atoms, e.g., an optionally substituted alkylene, alkenylene, alkylyne, cycloalkyl, alkylcycloalkyl, alkylarylalkyl chain of 2 to 20 atoms optionally with 1-4 heteroatoms selected from —O—, —NH—, and —S—. Illustrative examples of L are a single or double covalent bond, C1-12 alkylene, substituted C1-12 alkylene, C1-12 alkenylene, substituted C1-12 alkenylene, C1-12 alkynylene, substituted C1-12 alkynylene, $X_n$-phenyl-$Y_n$, or $X_n$-(phenyl)$_2$-$Y_n$, wherein X and Y are independently C1-6 alkylene, substituted C1-6 alkylene, C1-6 alkenylene, substituted C1-6 alkenylene, C1-6 alkynylene, substituted C1-6 alkynylene, or $S(O)_2$.

Illustrative P3/P3' groups include, without limitation:

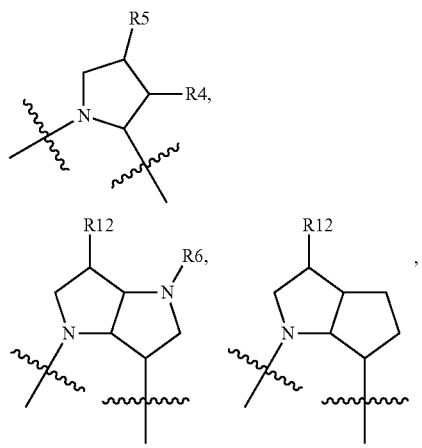

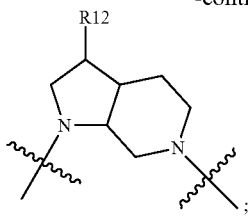

wherein $R^6$ is —H, C1-6 alkyl, substituted C1-6 alkyl, C1-6 alkoxy, substituted C1-6 alkoxy, C1-6 alkylsulfonyl, arylsulfonyl, cycloalkyl, substituted cycloalkyl, heterocycloalkyl, substituted heterocycloalkyl, aryl, substituted aryl, heteroaryl, or substituted heteroaryl; $R^4$, $R^5$, and $R^{12}$ are, independently, —H, —OH, C1-6 alkyl, C1-6 heteroalkyl, C1-6 alkoxy, aryloxy, cycloalkyl, heterocycloalkyl, aryl, C1-6 alkyl aryl, or heteroaryl, or C1-6 alkyl heteroaryl, optionally substituted in each case except when $R^4$ is —H or —OH.

As mentioned, in certain illustrative embodiments, the SMAC mimetic used in the practice of the invention is bivalent.

In certain illustrative embodiments, a selected SMAC mimetic inhibits XIAP-mediated caspase-3 repression and/ or degrades cIAP-1 not bound to TRAF2 (non TRAF2-bound, e.g., "cytoplasmic" cIAP-1 or "free" cIAP-1) as well as cIAP1 bound to TRAF2 and/or degrades cIAP-2 bound to TRAF2 but does not degrade cIAP-2 not bound to TRAF2 or weakly degrades cIAP-2 not bound to TRAF2 relative to degradation of cIAP-2 bound to TRAF2.

In certain illustrative embodiments, SMAC mimetics used in the practice of the current invention cause degradation of cIAP-2 not bound to TRAF2, but the extent of such degradation on a percentage basis is less than the extent of degradation of TRAF2-bound cIAP-2. The significance of the difference in effects of a SMAC mimetic on the cIAP-2 not bound to TRAF2, has been observed to correlate with the tolerability (or safety profile) of a SMAC mimetic in animals. If a first SMAC mimetic causes less degradation of cIAP-2 not bound to TRAF2, relative to degradation of TRAF2-bound cIAP-2, than a second SMAC mimetic, i.e., a structurally different SMAC mimetic, then the first SMAC mimetic is likely to be better tolerated in (i.e., more safely administered to) animals. More specifically, a skilled person can select two SMAC mimetics, each causing degradation of cIAP-1 not bound to TRAF2, TRAF2-bound cIAP-1 and TRAF2-bound cIAP-2 with one exhibiting a different (lesser) degree of degradation of cIAP-2 not bound to TRAF2, then the compound that causes less degradation of cIAP-2 not bound to TRAF2, is likely to be better tolerated with no significant loss in antitumor potency.

The degradation kinetics of non-TRAF2-bound cIAP-1, non-TRAF2-bound cIAP-2, TRAF2-bound cIAP-1 and TRAF2-bound cIAP-2 can be measured by western analysis. The extent of degradation can be observed visually in such assays over a period of time. For example, the extent of degradation of non-TRAF2-bound cIAP-2 and TRAF2-bound cIAP-2 may appear to be substantially the same immediately following treatment of cells with a SMAC mimetic but after several minutes, e.g., after 15 to 30 minutes, increased degradation of TRAF2-bound cIAP-2 relative to degradation of non-TRAF2-bound cIAP-2 may be observed in treated cells. Differences in extent of degradation can also be quantified. For example, in the case of western analysis using green fluorescence protein tagged cIAPs, the extent of degradation can be quantified using a device that measures the intensity of fluorescence.

For such SMAC mimetic, the extent of degradation of non-TRAF2-bound cIAP-2 will generally be less than 75% of (or about 75% of), i.e., about 75% or less than, the extent of degradation of TRAF2-bound cIAP-2 at relevant concentrations, for at least about 15 minutes, e.g., 30 to 120 minutes (or about 30 to about 120 minutes). The amount of SMAC mimetic used in such assay will vary with the potency of the SMAC mimetic but will generally be less than 1 µM, such as e.g., between about 1 and about 500 nM or between about 10 and about 150 nM In some cases, the extent of degradation of non-TRAF2-bound cIAP-2 will be less than 50% of (or about 50% of), i.e., about 50% or less than; or less than 25% of (or about 25% of), i.e., about 25% or less than; or less than 10% of (or about 10% of), i.e., about 10% or less than, the extent of the degradation of TRAF2-bound cIAP-2. For example, in a cIAP degradation assay with a SMAC mimetic having a cIAP degradation profile of the invention, TRAF2-bound cIAP-2 may be about 70-75% degraded after 30 minutes (i.e., only about 30% of the originally detected amount of TRAF2-bound cIAP-2 is still detectable); whereas non-TRAF2-bound cIAP-2 may only be about 35-40% degraded (i.e., 60% to 65% of the originally detected amount of non-TRAF2-bound cIAP-2 is still detectable) after 30 minutes. In this case, the SMAC mimetic is said to degrade non-TRAF2-bound cIAP-2 at about 50% or less than the extent of degradation of TRAF2-bound cIAP-2 (35% to 40% divided by (70% to 75%)=about 50%).

The induction of apoptosis is highly specific for susceptible tumours, whereas normal tissue appears to be spared. For instance, certain SMAC mimetics are capable of killing tumour cells in vitro in the picomolar concentration range, while having no effect on non-tumour cells in the 100 micromolar range.

Several SMAC mimetics have been developed that have significant anti-tumour activity in preclinical studies. Of those that have entered the clinic, birinapant (TL32711) is a potent bivalent small molecule SMAC mimetic. Birinapant is identified as Compound 15 in U.S. Pat. No. 8,283,372, the disclosure of which is included herein by cross-reference. In an embodiment, the IAP antagonist is birinapant.

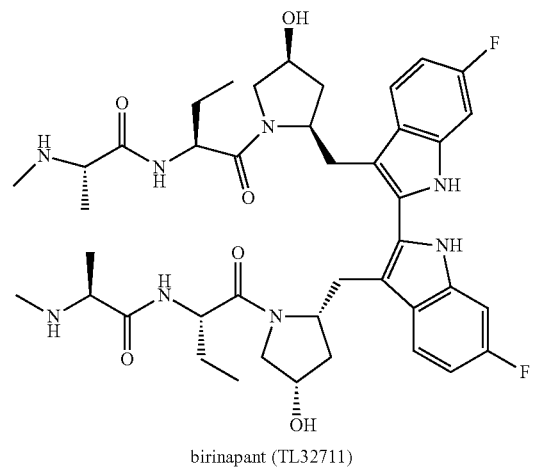 [SMILES: CC[C@H](NC(=O)[C@H](C)NC)C(=O)N1C[C@@H](O)C[C@H]1Cc1c(-c2[nH]c3cc(F)ccc3c2C[C@@H]2C[C@H](O)CN2C(=O)[C@H](CC)NC(=O)[C@H](C)NC)[nH]c2cc(F)ccc12]

birinapant (TL32711)

Additional information regarding the activity of birinapant and similar compounds is provided in U.S. Ser. No. 14/246,956, the disclosure of which is incorporated herein by reference.

Pharmaceutical compositions of SMAC mimetics and p38 and/or MK2 inhibitors may comprise a therapeutically effective amount of a compound as described above, or a pharmaceutically acceptable salt or other form thereof together with one or more pharmaceutically acceptable excipients. The phrase "pharmaceutical composition" refers to a composition suitable for administration in medical or veterinary use. The composition may also comprise additional active agents. For example the composition may include cytokines such as TNFα or small molecule inhibitors or antibiotics. It should be appreciated that the determinations of proper dosage forms, dosage amounts, and routes of administration for a particular patient are within the level of ordinary skill in the pharmaceutical and medical arts.

Compositions suitable for parenteral administration conveniently comprise a sterile aqueous preparation of a compound or composition of the invention, which is preferably isotonic with the blood of the recipient. This aqueous preparation may be formulated according to known methods using suitable dispersing or wetting agents, emulsifying and suspending agents. Various antibacterial and antifungal agents, for example, parabens, chlorobutanol, phenol, and sorbic acid also may be included. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Prolonged absorption of the injectable pharmaceutical form can be brought about by the use of agents delaying absorption, for example, aluminum monostearate and gelatin. Carrier formulation suitable for subcutaneous, intravenous, intramuscular, etc. administrations can be found in Remington's Pharmaceutical Sciences, Mack Publishing Co., Easton, Pa. which is incorporated herein in its entirety by reference thereto.

A pharmaceutical composition in intravenous unit dose form may comprise, e.g., a vial or pre-filled syringe, or an infusion bag or device, each comprising an effective amount or a convenient fraction of an effective amount such that the contents of one vial or syringe are administered at a time.

An effective dose is one that over the course of therapy, which may be, e.g., 1 or more weeks, results in treatment of the disorder, i.e., a decrease in the rate of disease progression, termination of disease. A useful starting point for determining the dosing regimen to be followed for administration of the IAP antagonist and the p38 inhibitor or the MK2 inhibitor (or both), is a dosing protocol that is employed for either agent alone. Useful dosing regimens for Birinapant are disclosed, e.g. in WO2013049350.

Solid dosage forms for oral administration include capsules, tablets, pills, powders, and granules. In such solid dosage forms, the compound is admixed with at least one inert pharmaceutically acceptable excipient such as (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, dragees, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Since one aspect of the present invention contemplates the treatment of the disease/conditions with a combination of pharmaceutically active agents that may be administered separately, the invention further relates to combining separate pharmaceutical compositions in kit form. The kit comprises a number of separate pharmaceutical compositions: one contains the SMAC mimetic used in the method of the present invention, and optionally a second one containing the p38 inhibitor and a third one containing MK2 inhibitor. Optionally the kit may contain addition separate pharmaceutical preparations. The kit comprises a container for containing the separate compositions such as a divided bottle or a divided foil packet. Additional examples of containers include syringes, e.g., pre-filled syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . . Second Week, Monday, Tuesday, . . . " etc. Other variations of memory aids will be readily apparent. A "daily dose" can be a single tablet or capsule or several pills or capsules to be taken on a given day. Also, a daily dose of a substance of the present invention can consist of one tablet or capsule, while a daily dose of the second substance can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Liquid dosage forms for oral administration include pharmaceutically acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

The compounds and compositions used in the method of the present invention also may benefit from a variety of delivery systems, including time-released, delayed release or sustained release delivery systems. Such option may be particularly beneficial when the compounds and composition are used in conjunction with other treatment protocols as described in more detail below.

Many types of controlled release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active compound for at least 30 days, and preferably 60 days. Long-term sustained release implants are well-known to those of ordinary skill in the art and include some of the release systems described above.

IAP antagonists also include molecules that reduce the expression of an IAP gene, such as cIAP1, cIAP2 or XIAP. Suitable antagonists that are capable of reducing the expression of an IAP gene would be known to persons skilled in the art.

In a similar manner p38 and MK2 inhibitors include molecules that reduce the expression of a p38 or MK2 gene. Suitable antagonists that are capable of reducing the expression of a p38 or MK2 gene would be known to persons skilled in the art.

Examples of molecules that interfere with the expression of the target gene include nucleic acid molecules, such as RNA or DNA molecules (including double-stranded or single-stranded), and peptides, such as antisense peptide nucleic acids.

Useful DNA molecules include antisense, as well as sense (e.g. coding and/or regulatory) DNA molecules. Antisense DNA molecules include short oligonucleotides. Persons skilled in the art would be able to design suitable short oligonucleotides for use in accordance with the present invention. Examples are XIAP antisense oligonucleotide AEG35156 (Carter et al., 2011), cIAP1 antisense oligonucleotide (McEleny et al., 2004), p38 antisense oligonucleotide (Duan et al., 2005). Other examples of useful DNA molecules include those encoding interfering RNAs, such as shRNA and siRNA. Yet another example is catalytic DNA molecules known as DNAzymes.

Useful RNA molecules capable of reducing the expression of an IAP gene, also referred to herein as RNA interference molecules, include siRNA, dsRNA, stRNA, shRNA, and miRNA (e.g., short temporal RNAs and small modulatory RNAs), ribozymes, and guide or CRISPR RNAs used in combination with the Cas or other nucleases (van der Oost et al., 2014).

RNA interference (RNAi) is particularly useful for specifically inhibiting the production of a particular protein. Although not wishing to be limited by theory, Waterhouse and collaborators have provided a model for the mechanism by which dsRNA can be used to reduce protein production (Waterhouse et al., 1998). This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering WO 99/32619, WO 99/53050, WO 99/49029, WO 01/34815 and (Waterhouse et al., 1998), (Smith et al., 2000).

In one example, a DNA is introduced that directs the synthesis of an at least partly double stranded RNA product (s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from the cell that destroys both the double stranded RNA and also the homologous RNA transcript from the target gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ('siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the cell in which it is to be introduced, e.g., as determined by standard BLAST search.

Synthesis of RNAi molecules suitable for use with present invention can be effected by first scanning the mRNA sequence of the target downstream of the AUG start codon for AA dinucleotide sequences. Occurrence of each AA and the 3' adjacent 19 nucleotides is recorded as potential siRNA target sites. Preferably, siRNA target sites are selected from the open reading frame. Second, potential target sites are compared to an appropriate genomic database using any sequence alignment software, such as BLAST. Putative target sites which exhibit significant homology to other coding sequences are filtered out. Qualifying target sequences are selected as template for SiRNA synthesis. Preferred sequences are those including low G/C content as these have proven to be more effective in mediating gene silencing as compared to those with G/C content higher than 55%. Several target sites are preferably selected along the length of the target gene for evaluation.

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see for example (Almeida and Allshire, 2005; Millar and Waterhouse, 2005; Pasquinelli et al., 2005).

DNAzymes are single-stranded polynucleotides which are capable of cleaving single and double stranded polynucleotides which are capable of cleaving both single and double stranded target sequences (Breaker and Joyce, 1995; Santoro and Joyce, 1997). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Khachigian, 2002; Santoro and Joyce, 1997).

Examples of construction and amplification of synthetic, engineered DNAzymes recognizing single and double-stranded target cleavage sites have been disclosed in U.S. Pat. No. 6,326,174 to Joyce et al.

The terms "double stranded RNA" or "dsRNA" refer to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA, comprises a dsRNA molecule.

Other suitable RNA interference molecules include unmodified and modified double stranded (ds) RNA molecules including, short-temporal RNA (stRNA), small interfering RNA (siRNA), short-hairpin RNA (shRNA), microRNA (miRNA) and double-stranded RNA (dsRNA). The dsRNA molecules (e.g. siRNA) also may contain 3' overhangs, such as 3'UU or 3'TT overhangs.

In an embodiment, the siRNA molecules of the present invention have a double stranded structure. In an embodiment, the siRNA molecules of the present invention are double stranded for more than about 25%, more than about 50%, more than about 60%, more than about 70%, more than about 80%, more than about 90% of their length.

As used herein, "gene silencing" induced by RNA interference refers to a decrease in the mRNA level in a cell for a target gene (e.g., cIAP1 gene and/or cIAP2 gene) by at least about 5%, about 10%, about 20%, about 30%, about 40%, about 50%, about 60%, about 70%, about 80%, about 90%, about 95%, about 99%, about 100% of the mRNA level found in the cell in the absence of RNA interference.

The RNA interference molecules also include modified RNA molecules having one or more non-natural nucleotides; that is, nucleotides other than adenine "A", guanine "G", uracil "U", or cytosine "C". A modified nucleotide residue or a derivative or analog of a natural nucleotide may also be used. Any modified residue, derivative or analog may be used to the extent that it does not eliminate or substantially reduce (by at least 50%) RNAi activity of the molecule. Examples of suitable modified residues include aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH2 UTP, 2'NH2 CTP, and 2'F. UTP. Suitable modified nucleotides also include aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH2 uridine, 2'NH2 cytidine, and 2'F uridine, including the free pho (NTP) RNA molecules, as well as all other useful forms of the nucleotides.

RNA interference molecules may also contain modifications in the ribose sugars, as well as modifications in the phosphate backbone of the nucleotide chain. For example, siRNA or miRNA molecules containing α-D-arabinofuranosyl structures in place of the naturally-occurring α-D-ribonucleosides found in RNA can be used as RNA interference molecules according to the present invention. Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly α-arabinose. Phosphorothioate linkages can also be used to stabilize the siRNA and miRNA molecules.

An "siRNA" refers to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In an embodiment, an siRNA refers to a nucleic acid that has substantial or complete identity to a target gene and forms a double stranded siRNA. The sequence of the siRNA can correspond to the full length target gene, or a subsequence thereof.

In an embodiment, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

Suitable siRNAs also include small hairpin (also called stem loop) RNAs (shRNAs). In an embodiment, the shRNA comprises short, e.g. about 19 to about 25 nucleotide, antisense strand, followed by a nucleotide loop of about 5 to about 9 nucleotides, and the analogous sense strand. Alternatively, the sense strand may precede the nucleotide loop structure and the antisense strand may follow.

In an embodiment, the antagonist of IAP is siRNA, shRNA or miRNA. In further embodiments the inhibitor of p38 or MK2 is siRNA, shRNA or miRNA.

Specific RNA interference molecules, such as siRNA, shRNA and miRNA molecules, can be easily designed by one skilled in the art having regard to the sequence of the target gene.

In an embodiment, the IAP antagonist siRNA, shRNA or miRNA is targeted against a sequence selected from the group consisting of NCBI Reference Sequence: NM_001166.4, NCBI Reference Sequence: NM_001256163.1, NCBI Reference Sequence: NM_001256166.1, GenBank: DQ068066.1, NCBI Reference Sequence: NM_001165.4, NCBI Reference Sequence: NM_182962.2, GenBank: BC037420.1, NCBI Reference Sequence: NM_001167.3, NCBI Reference Sequence: NM_001204401.1, NCBI Reference Sequence: NR_037916.1, and NCBI Reference Sequence: NG_007264.1.

In an embodiment, the p38 antagonist siRNA, shRNA or miRNA is targeted against a sequence selected disclosed in p38α(MAPK14) ACCESSION NM_001315 or p3813 (MAPK11) ACCESSION NM_002751.

In an embodiment, the MK2 antagonist siRNA, shRNA or miRNA is targeted against a sequence selected disclosed in MK2 (MAPKAPK2) ACCESSION NM_004759, Other RNA molecules which are single stranded, or are not considered to be RNA interference molecules, may also be useful as therapeutic agents in accordance with the present invention, including messenger RNAs (and the progenitor pre-messenger RNAs), small nuclear RNAs, small nucleolar RNAs, transfer RNAs and ribosomal RNAs.

IAP antagonists capable of reducing the expression of an IAP gene, as herein described (e.g., RNA interference molecules such as siRNA, dsRNA, stRNA, shRNA, and miRNA), can be administered to the subject in need thereof by any suitable means and route of administration, as would be known to persons skilled in the art (e.g., gene therapy or gene delivery methods). It would be understood that the IAP antagonist is to be administered to a subject in such a way as to ensure that the antagonist is able to contact and enter a cell in the subject, whether the cell is infected with the pathogen or is at least capable of becoming infected with the pathogen. Examples of suitable routes of administration include intravenous, intramuscular, topical, oral, intranasal or by gene gun or hypospray instrumentation.

In an embodiment of the present invention the IAP antagonist is administered in combination with a p38 inhibitor preferably selected from the group consisting of LY222820, SCIO-469, BIRB 796, VX-702, SB 239063, SB202190, BMS 582949, SB203580, GW856553X, Skepinone-L, PH-797804, VX-745, TAK-715, JX-401, CAY10571, SB220025, AMG 548, ML 3403, SKF 86002, SX 011, SB-681323, SB 242235, CMPD-1, DBM 1285 dihydrochloride, EO 1428 and RWJ 67657.

In another embodiment of the present invention the IAP antagonist is administered in combination with a MK2 inhibitor, preferably selected from the group consisting of PF-3644022, PHA 767491, MK-2 Inhibitor III and MK-2 Inhibitor IV.

The IAP antagonist and the p38 and/or MK2 inhibitor may be administered together in a single pharmaceutical preparation or in separate pharmaceutical preparations. The discussion above relating to pharmaceutical preparations and routes of administration apply equally to the IAP antagonist, p38 inhibitor and MK2 inhibitor.

The present invention is applicable to the treatment of a wide range of proliferative disorders, including but not limited to the following cancers: pancreatic cancer, ovarian cancer, breast cancer, mesothelioma, peripheral neuroma, glioblastoma, melanoma, adrenocortical carcinoma, AIDS-related lymphoma, anal cancer, bladder cancer, meningioma, glioma, astrocytoma, breast cancer, cervical cancer, chronic myeloproliferative disorders, colon cancer, endometrial cancer, ependymoma, esophageal cancer, Ewing's sarcoma, extracranial germ cell tumors, extrahepatic bile duct cancer, gallbladder cancer, gastric cancer, gastrointestinal carcinoid tumors, gestational trophoblastic tumors, hairy cell leukemia, Hodgkin lymphoma, non-Hodgkin lymphoma, hypopharyngeal cancer, islet cell carcinoma, Kaposi sarcoma, laryngeal cancer, leukemia, lip cancer, oral cavity cancer, liver cancer, male breast cancer, malignant mesothelioma, medulloblastoma, Merkel cell carcinoma, metastatic squamous neck cell carcinoma, multiple myeloma and other plasma cell neoplasms, mycosis fungoides and the Sezary syndrome, myelodysplastic syndromes, nasopharyngeal cancer, neuroblastoma, non-small cell lung cancer, small cell lung cancer, oropharyngeal cancer, bone cancers, including osteosarcoma and malignant fibrous histiocytoma of bone, paranasal sinus cancer, parathyroid cancer, penile cancer, pheochromocytoma, pituitary tumors, prostate cancer, rectal cancer, renal cell cancer, retinoblastoma, rhabdomyosarcoma, salivary gland cancer, small intestine cancer, soft tissue sarcoma, supratentorial primitive neuroectodermal tumors, pineoblastoma, testicular cancer, thymoma, thymic carcinoma, thyroid cancer, transitional cell cancer of the renal pelvis and ureter, urethral cancer, uterine sarcoma, vaginal cancer, vulvar cancer, and Wilm's tumor and other childhood kidney tumors.

Whilst the present invention is applicable to a range of cancers it is preferred that the cancer is selected from AML, myelodysplastic syndromes, myeloproliferative syndromes, multiple myeloma, ALL, ovarian cancer, colorectal cancer and breast cancer.

The present invention also provides use of a combination of an IAP antagonist and a p38 or MK2 inhibitor, or both a p38 inhibitor and a MK2 inhibitor, for the treatment of cancer in a subject.

The method of the present invention may further comprise the administration of one or more additional therapeutic agents.

The IAP antagonist can be delivered to a subject in need thereof by any suitable means known to persons skilled in the art. For example, persons skilled in the art would understand that, where the IAP antagonist is an RNA interference molecule, the method of administration would need to facilitate the delivery of the IAP antagonist to the cell cytoplasm where it can interact with the target sequence. Where the IAP antagonist is an siRNA molecule, the RNA interference molecule may be delivered to a subject by the co-administration of a hepatocyte-targeted, N-acetylgalactosamine-conjugated melittin-like peptide (NAG-MLP) with a liver-tropic cholesterol-conjugated siRNA (Wooddell et al., 2013). Where the molecule is an antisense DNA oligonucleotide molecule, it may be delivered to a subject in need thereof by the method described by Janssen and collaborators (Janssen et al., 2013).

In an alternative embodiment gene therapy may be conducted on the subject to decrease the expression of or inactivate one or more IAP genes in the subject.

As opposed to direct administration of the IAP antagonist it can be produced in vivo by delivery of a nucleotide encoding the IAP antagonist. An example of this approach is described in Pan et al, 2014 where a vaccinia virus carrying the SMAC/DIABLO gene was used to infect and destroy hepatocellular carcinoma (Pan et al., 2014). Such a treatment modality is often referred to as "gene therapy". For example, polynucleotides encoding a SMAC mimetic may be employed in gene therapy techniques for the treatment of cancer.

In one form a polynucleotide encoding a SMAC mimetic may be engineered for expression in a replication defective retroviral vector or adenoviral vector or other vector (e.g. poxvirus vectors). The engineered virus is then allowed to infect tumour cells and express the SMAC mimetic leading to tumour cells death. It is intended that the current invention extends to gene therapy delivery of the therapeutic agents of the current invention.

The method of delivery includes the use of solutions and suspensions that are administrable to the subject. Suitable modes of administration would be known to persons skilled in the art. Examples include intravenous, subcutaneous, intramuscular or intraperitoneal.

The subject in which the cancer is to be treated may be a human or a mammal of economical importance and/or social importance to humans, for instance, carnivores or omnivores other than humans (such as cats and dogs), swine (pigs, hogs, and wild boars), ruminants (such as cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are also of economical importance to humans. The term "subject" does not denote a particular age. Thus, both adult and newborn subjects are intended to be covered.

The present invention also provides use of a combination of an IAP antagonist and a p38 and/or a MK2 inhibitor in the manufacture of a medicament for the treatment of cancer in a subject.

The medicament may include further amounts of pharmaceutically acceptable and suitable carriers, diluents, or excipients. These include all known solvents, dispersion media, fillers, solid carriers, castings, antifungal and anti-bacterial agents, surfactants, isotonic and absorption agents and the like. It will be understood that the medicament may also include one or more additional therapeutic agents (i.e., in addition to the IAP antagonist), as herein described.

The present invention also contemplates co-formulation and/or co-administration with other pharmaceutically active agents including, without limitation, TNFα agonists such as TNFα, TRAIL (TNF-related apoptosis inducing ligand) or TRAIL agonists such as but not limited to TRAIL receptor antibodies.

Those skilled in the art will appreciate that the invention described herein is susceptible to variations and modifications other than those specifically described. It is to be understood that the invention includes all such variations and modifications, which fall within the spirit and scope. The invention also includes all of the steps, features, compositions and compounds referred to or indicated in this specification, individually or collectively, and any and all combinations of any two or more of said steps or features.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

EXAMPLES

Materials and Methods
Reagents

SMAC mimetic compounds, Compound A (GT12911), GT13072 and Birinapant (TL32711) were synthesized by TetraLogic Pharmaceuticals. P38 inhibitor LY222820, JNK1/2 inhibitor JNK-IN-8 and MEK1/2 inhibitor PD0325901 were purchased from Selleckchem, p38 inhibitor SCIO-469 and MK2 inhibitor PF-3644022 were purchased from Tocris Bioscience. Kinase inhibitors library was purchased from Synthesis Med Chem.

Cell Culture and Cell Death

BMDMs from C56/B16, p38α$^{LysMCre}$ or Mk2$^{-/-}$ were cultured for 6 days in DMEM+10% FBS (v/v)+20% L929 mouse fibroblasts (a source of macrophage colony stimulating factor), plated and assayed the following day. BMDMs cells were seeded and assayed in the presence of L929 conditioned medium. AML cells were cultured in IMDM+10% FBS (v/v)+2.5 ng/ml of IL-3. NCI-H929 cells were cultured in RPMI+10% FBS (v/v). Cell suspension from breast ER+ patient derived tumours was cultured in mammosphere media. After treatment with SMAC mimetic with or without kinases inhibitors cell viability was measured by staining with propidium iodide (2 μg/mL) or by using CellTiter-Glo® (Promega).

Kinase Inhibitors Screen 100 000 BMDM per well were seeded in a 96 well plates. Cells were pretreated 30 min with 12 p38 inhibitors and then treated with 500 nM of SMAC mimetic Compound A for 24 h. Supernatant were harvested to measure TNFα content by ELISA.

Cytokine Measurement

ELISAs for the measurement of the concentrations of TNFα were performed following the manufacturers instructions (eBioscience).

Immunoblot Analysis.

Whole cell lysates were prepared using DISC buffer (1% NP-40, 10% glycerol, 150 mM NaCl, 20 mM Tris pH 7.5, 2 mM EDTA, Roche complete protease inhibitor cocktail, 2 mM sodium orthovanadate, 10 mM sodium fluoride, β-glycerophosphate, N2O2P07). Proteins in cell lysates were subjected to polyacrylamide gel electrophoresis on 4-12% gradient NuPAGE Bis-Tris gels (Life Technologies) in XCell SureLock™ Midi-Cell apparatus (Life Technologies) and transferred on to Immobilon-P PVDF membranes (Bio-Rad). Membranes were blocked and antibodies diluted in 5% skim milk powder/0.2% Tween20/phosphate buffered saline. Antibodies against the following proteins were used for immunoblotting: phospho-JNK1/2, phospho-ERK1/2, phospho-MK2, JNK1/2, ERK1/2, MK2 (Cell Signaling), cIAP1 (Enzo) and β-actin (loading control; Sigma Aldrich) were detected by chemoluminescence (Millipore) after incubation with secondary antibodies conjugated to HRP.

Tolerability of SMAC Mimetic Plus p38 Inhibitor

To assess the safety of SMAC mimetic plus p38 inhibitor in human cells, peripheral blood was collected from healthy donors following informed consent and in accordance with the guidelines approved by the Alfred Hospital Human Research Ethics Committee. Mononuclear cells were isolated by Ficoll-Paque Plus (GE Healthcare) sedimentation and enumerated using Trypan-blue exclusion. Cells were seeded at $0.2-1\times10^6$ cells per ml in Stemspan SFEM II medium (Stem Cell Technologies) supplemented with 100 ng/ml rhFlt-3L, 100 ng/ml rhSCF, 20 ng/ml rhIL-3, 20 ng/ml rhIL-6, 100 IU/ml DNase I and penicillin/streptomycin; then treated with 250 nM of birinapant±1 µM of LY2228820 for 48 h at 37° C., 5% CO2. Following incubation, cell death was determined using flow cytometry via hCD34.PE (Beckman Coulter) and PI staining. Samples were acquired using a FACSCanto™ II (Becton Dickonson) and analysed using FlowJo vX.0.7 software (Tree Star, Inc.). All samples were tested in at least 2-3 independent experiments.

To assess the safety of SMAC mimetic plus p38 inhibitor C57BL6 mice were injected by intra-peritoneal route twice a week for 4 weeks with either vehicle (6% Captisol) or 15 mg/kg of LY222820 or 5 mg/kg birinapant±15 mg/kg LY2228820, or 10 mg/kg birinapant±15 mg/kg LY2228820. Another cohort received either vehicle or 5 mg/kg of GT13072, or 15 mg/kg of LY222820 or combination.

Blood Cell Analysis

200 µL of blood was collected from the retro-orbital plexus into tubes containing potassium ethylenediaminetetraacetic acid (Sarstedt) and analyzed in an Advia 2120 automated hematologic analyzer (Bayer).

Statistic Analysis

Unless otherwise specified, data are presented as mean±SEM. Comparisons were performed with a Student's t test with * $p\leq0.05$;  $p\leq0.01$; * $p\leq0.005$*; ** $p\leq0.001$; *** $p\leq0.0005$.

In Vivo Treatment

To assess the anti-tumour efficacy of SMAC mimetic plus p38 inhibitor C57BL6 Albinos mice were injected by intravenous route with $5\cdot10^5$ MLLENLluc. Luciferase activity was measured at D4 and D8 after leukemic cells injection to ensure engraftment. Treatment started at D8. Mice were treated twice a week for 4 weeks with either vehicle (6% Captisol), 5 mg/kg of Birinapant, or 10 mg/kg of LY222820 or combination. Mice were monitored for leukemia progression once a week using the in vivo bioluminescent imaging. Bioluminescent imaging was performed using an IVIS 100 imaging system (Caliper LifeSciences). Mice were injected intraperitoneally with 150 mg/kg D-Luciferin (Caliper LifeSciences), anesthetized with isoflurane, and imaged for 1 min after a 15-min incubation following injection. For MLLAF9 $5\times10^5$ leukemic cells were i.v. injected into C57BL6 mice and treatment started at day 3 Animal technicians blinded to treatment conditions sacrificed the mice on ethical grounds, without any input from the experimental investigator, at terminal disease. Parameters used to determine terminal disease were weight loss, enlarge spleen, anaemia, lethargy, hunched posture and leg paralysis.

Example 1: Combination of SMAC Mimetic and Kinase Inhibitors

The apoptotic activity of SMAC mimetics as single agents is believed to be due to degradation of cIAP1&2 and autocrine production of TNF. Consistent with this, cells that can be induced to secrete TNFα upon treatment with SMAC mimetic are efficiently killed by it as a single agent, and some cell lines that are not killed by SMAC mimetics alone do die when SMAC mimetics is combined with exogenously added TNFα. These observations suggest that SMAC mimetics-induced TNFα production is a key requirement for its ability to kill cancer cells as a single agent. The exact molecular mechanisms involved in this process are unclear, in particular why some cell types produce autocrine TNF when IAPs are depleted by SMAC mimetics, whereas other cell types do not. Analysis of mutant mice lacking genes for various components of the NF-κB (e.g. p65 NF-κB2 and p52 NF-κB2) and related signalling pathways suggested that NF-κB collaborates with other signalling pathways (such as MAP kinase pathways) to regulate the TNFα production induced by SMAC mimetics.

To find out which other pathways might be involved, the present inventors screened 139 kinase inhibitors to identify those that promoted the induction of TNFα secretion in response to SMAC mimetics. Surprisingly, of the 12 p38 inhibitors tested, 11 significantly increased TNFα production induced by SMAC mimetic (FIG. 1A). Furthermore, the p38 inhibitor LY2228820 increased TNF production of three different smac-mimetics (e.g CompA, GT13072 and birinapant) (FIG. 1B). Most importantly, the p38 inhibitors LY2228820, VX-702, VX-745 and TAK-715 and the MK2 inhibitor PF-3644022 dramatically increased cell death induced by SMAC mimetics in a dose dependant manner and at therapeutically achievable concentrations (FIG. 1C).

These results were unexpected given the role of p38 pathway in TNFα expression in response to Toll-Like Receptors (TLRs). Indeed, upon TLR activation, p38 induces a phosphorylation cascade involving kinases and transcription factors leading to TNF transcription and secretion (Gaestel, 2013).

Figure 2:
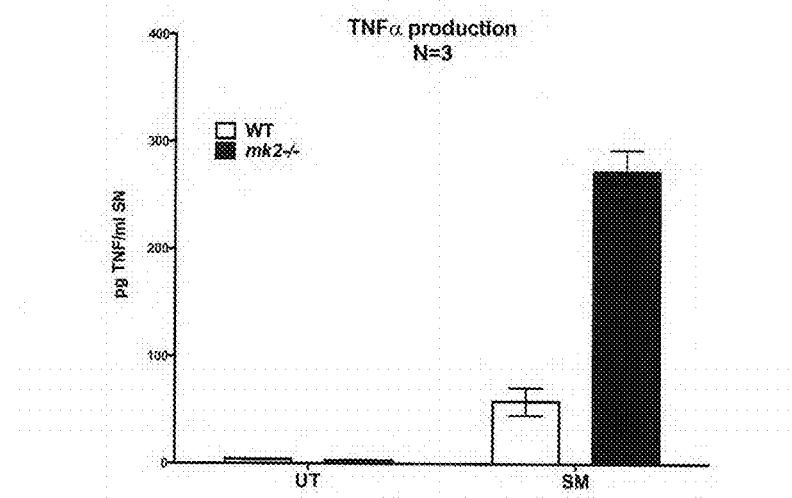
FIG. 2: p38/MK2 pathway negatively regulates TNF production induced by SMAC mimetics. Wild type, p38 (A) and MK2 knock-out (B) BMDM were treated with indicated concentrations of SMAC mimetic Compound A (SM) for 24 h, and TNFα quantified as in FIG. 2A. N=3-4 biological repeats and error bars are SEM.
Figure 2:
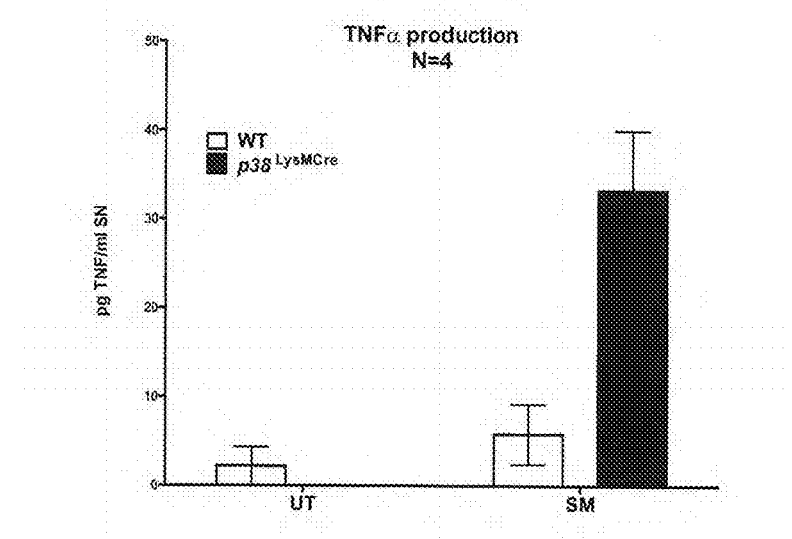

The kinase MK2 has been demonstrated to be the downstream mediator of p38 that serves to activate TNFα transcription in response to TLRs (Gaestel, 2013). To better understand the role of the p38/MK2 pathway in the TNFα production induced by SMAC mimetics, the present inventors challenged BMDMs from p38 and MK2 knock-out mice with SMAC mimetic. It was found that in the absence of p38 or MK2, BMDM produced greater amounts of TNFα in response to SMAC mimetic Compound A (FIGS. 2A&B). This unexpected result is nonetheless consistent with those obtained with the 11 p38 inhibitors, and suggests that the effects of those kinase inhibitors are on-target effects.

Figure 3:
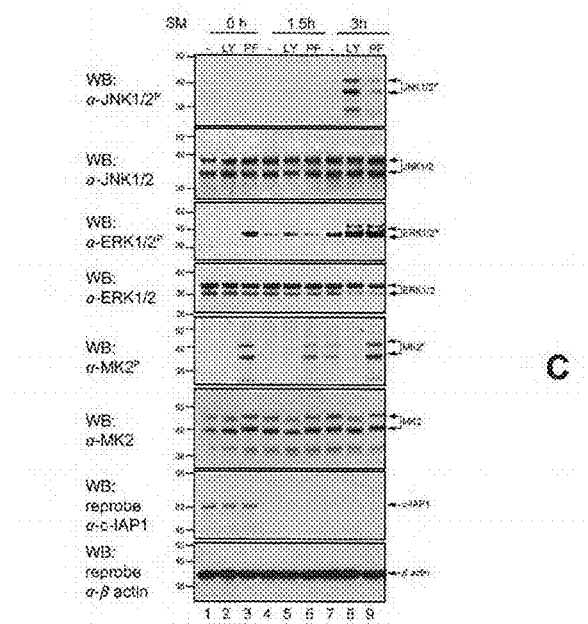
FIG. 3: p38 inhibition increases SMAC mimetic-induced TNFα production through ERK1/2 and JNK1/2 activation. A. Immuno-analysis of BMDM treated with 500 nM SMAC mimetic Compound A (SM) for indicated times ±1 μM of p38 inhibitor LY2228820 or ±1 μM of MK2 inhibitor PF-3644022. B and C. wild type (wt), p38$^{LysMCre}$ or Mk2$^{-/-}$ BMDM were treated with 100 nM of CompA (SM)±indicated concentrations of JNK1/2 inhibitor JNK-IN-8 (B) or MEK1/2 inhibitor PD0325901 (C) for 6 h. TNFα production was measured by ELISA of supernatants. N=3 biological repeats and error bars are SEM.
Figure 3:
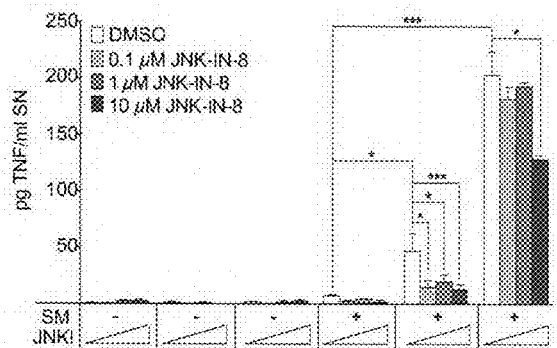
Figure 3:
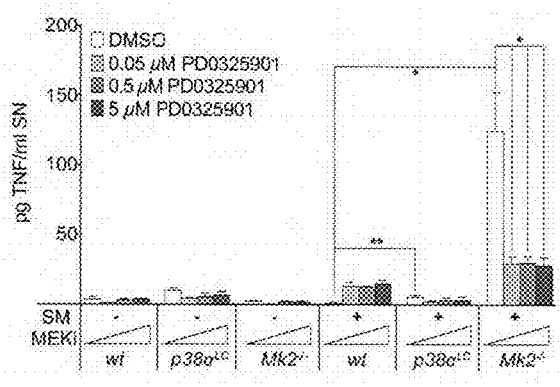

Example 2: ERK1/2 and JNK1/2 Activities in Response to SMAC Mimetic and p38 Inhibition The p38 pathway regulates key cellular signalling related to inflammation. Its crucial role in inflammatory cytokine expression has been exploited to develop p38 inhibitors to inhibit TNF production in auto-immune diseases. To date, several orally active p38 inhibitors have entered clinical trials (Cohen and Alessi, 2013). However, despite encouraging preclinical findings, none of these compounds advanced to late stage clinical trials due to lack of efficacy and/or unacceptable side effects[18]. In recent years, several potential reasons have come to light to explain why p38 may not be an optimal target for the development of anti-inflammatory drugs. For example, p38 participates in feed-back control loops that suppress the activities of 'upstream' MAPK, implicated in the activation of the MAPK JNKs, which stimulate the production of TNFα during inflammatory processes. Therefore, drugs that inhibit p38 cancel these feedback control loops, leading to a hyperactivation of JNKs and a consequent increase in pro-inflammatory cytokines that may contribute to the modest clinical responses and hepatic toxicities (Cohen and Alessi, 2013). Consistent with this, the present inventors found that cells treated with p38 inhibitor and MK2 inhibitor increased JNK1/2 phosphorylation in response to SMAC mimetic (FIG. 3A). The kinases JNK1 and 2 have been reported to directly regulate the transcription of TNF in many stimuli. Accordingly, cells that were treated with JNK1/2 inhibitor had considerably decreased TNF production of SM-treated p38α$^{LysMCre}$ and Mk2$^{-/-}$ cells (FIG. 3B). In addition of an increase of phospho-JNK1/2, the inventors found that inhibition of p38 or MK2 increased phospho-ERK1/2 in SM-treated cells (FIG. 3A). Similarly to JNK inhibitor, ERK inhibitor was able to abolish TNF production in p38α$^{LysMCre}$ and Mk2$^{-/-}$ SM-treated cells (FIG. 3C). This suggests that p38 inhibition increased TNFα and tumour-cell death induced by SMAC mimetic through JNK1/2 and ERK1/2 activation.

Example 3: Co-Administration of SMAC Mimetics and p38 and MK2 Inhibitors in Cancerous Cells While p38 inhibitors are no longer considered to be the ideal drug to treat inflammatory diseases, they are currently being trialed to treat cancer. For instance, Scios has developed an orally active p38 inhibitor Talmapimod (SCIO-469) that has completed a Phase I/II study in patients with low- and intermediate-1-risk Myelodysplastic syndromes. The study revealed that oral Talmapimod administration is well tolerated but only one patient achieved a complete remission that persisted for more than 2 years (Sokol et al., 2012). The use of p38 inhibitors as single agents in cancer therapy therefore appears likely to only give a modest clinical response. Nevertheless, in vitro studies have provided evidence of a potential use of these compounds when combined with other anti-tumor agents (Ishitsuka et al., 2008; Navas et al., 2006). Accordingly, Talmapimod and LY2228820 are undergoing Phase I/II clinical studies in combination with bortezomib, carboplatin, gemcitabine to treat multiple myeloma and ovarian cancer (ClinicalTrails.gov, NCT01663857, NCT00095680, NCT00087867).

Several report have shown that IAPs may be suitable therapeutic targets to treat different types of cancer such AMLs, myelodysplastic syndromes and multiple myeloma (Hess et al., 2007; Tamm et al., 2000; Tamm et al., 2004; Yamamoto et al., 2004). Consequently, a phase I/II clinical trial has been initiated to evaluate Birinapant as a single drug in relapsed elderly AML and myelodysplastic syndromes patients (ClinicalTrials.gov, NCT01486784). However, the present inventors have found that in vitro some human AML patient samples did not respond to Birinapant treatment. It is therefore unlikely that Birinapant as a single agent will cure all types of AML.

Figure 4:
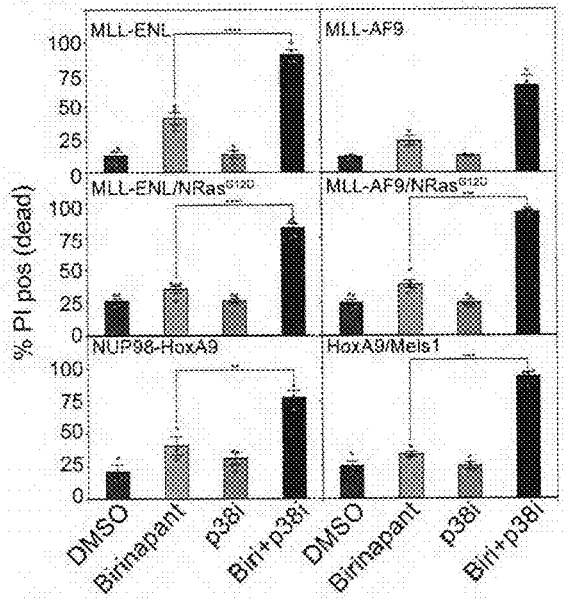
FIG. 4: p38 inhibitors and MK2 inhibitors sensitized primary murine AMLs to SMAC mimetic. Cells were treated with birinapant at 50 nM for MLL-ENL, 100 nM for NUP98-HOXA9, 250 nM for MLLAF9, 500 nM for MLLENL/Ras$^{G12D}$, MLLAF9/Ras$^{G12D}$ and HOXA9/Meis1±1 μM of p38 inhibitors LY2228820 (A) or SCIO-469 (B) or ±1 μM MK2 inhibitor PF-364402 (B) for 24 h. Cell death was measured by flow cytometry after PI staining of the cells 24 h post treatment. N=3-5 independent tumours. Error bars are SEM.
Figure 4:
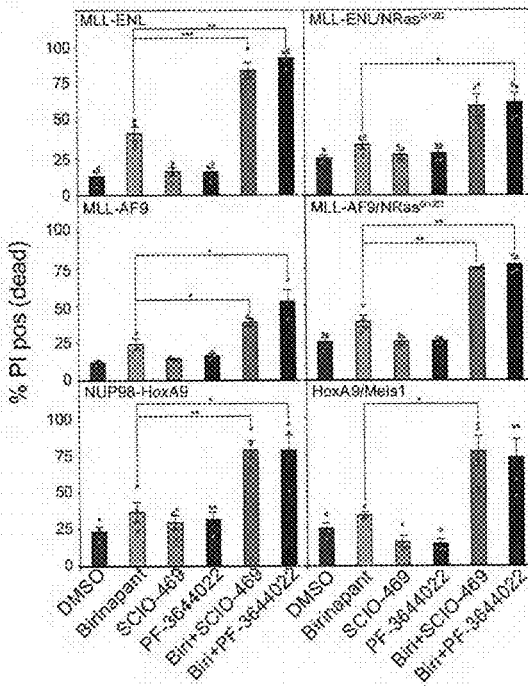

To assess the efficacy of the combined therapy several murine AML models that accurately reflect the genetics and pathology of human AMLs were used. Indeed, transduction and transplantation of hematopoietic stem/progenitor cells with combined oncogenic components often found in human AMLs into syngeneic recipients, results in aggressive and transplantable leukemia that recapitulate human AML. Most importantly, those AML mouse models can predict the behaviour of therapeutic agents used in the clinic (Zuber et al., 2009). The present inventors generated MLL-ENL+/–mutated Ras, MLL-AF9+/–mutated Ras, NUP98-HOXA9 and HOXA9/Meis1 AML mouse models and examined their responses to the association of Birinapant with p38 and with MK2 inhibitors. It was found that the inhibition of p38/MK2 pathway using p38 and MK2 inhibitors significantly increased cell death induced by Birinapant in all AML type tested (FIG. 4).

Figure 5:
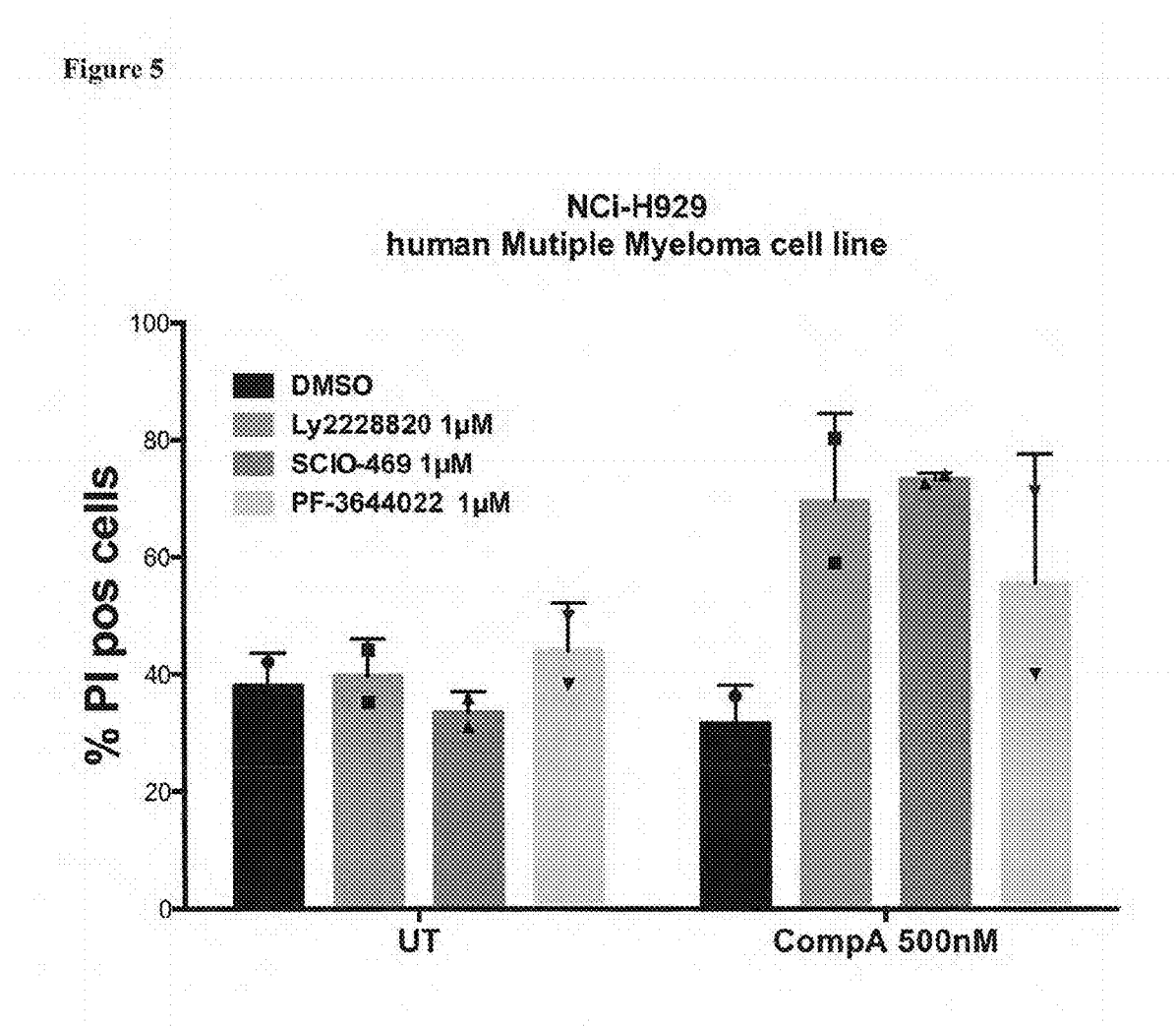
FIG. 5: p38 inhibitors and MK2 inhibitors sensitized human multiple myeloma to SMAC mimetic. NCI-H929 cells were treated with 500 nM of Compound A ±1 μM of p38 inhibitors (LY2228820 or SCIO-469) or ±1 μM MK2 inhibitor (PF-364402) for 24 h. Cell death was measured by flow cytometry after PI staining of the cells 24 h post treatment. N=2 independent experiments. Error bars are SD.

The present inventors also tested the efficacy of the combined therapy in the multiple myeloma derived cell line NCI-H929. It was found that the inhibition of p38/MK2 pathway using p38 and MK2 inhibitors significantly increased tumour-cell death induced by the pre-clinical SMAC mimetic compound A in NCI-H929 cells (FIG. 5)

Figure 6:
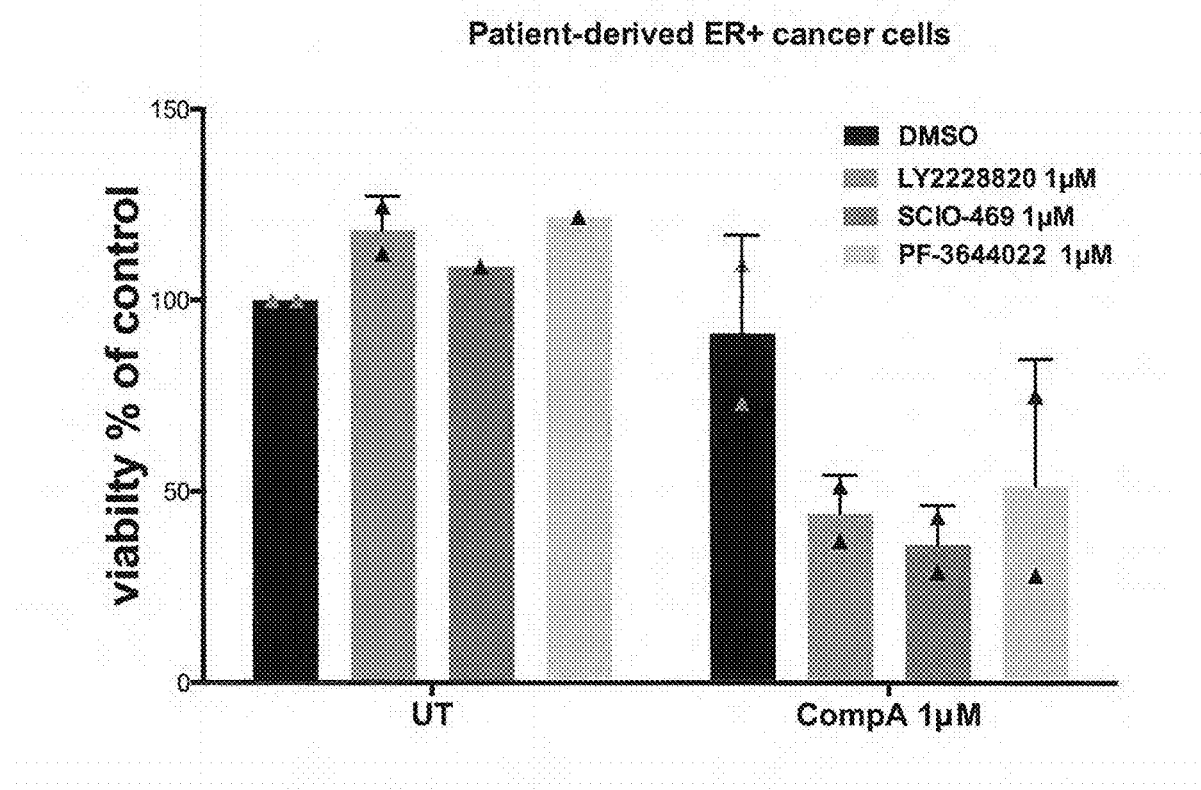
FIG. 6: p38 inhibitors and MK2 inhibitors sensitized primary human breast cancer to SMAC mimetic. Patient-derived xenograft breast tumor cells were treated with 1 μM of Compound A ±1 μM of p38 inhibitors (LY2228820 or SCIO-469) or ±1 μM MK2 inhibitor (PF-364402) for 24 h. Cell viability was measured after 24 h of treatment using CTG reagent. N=2 independent experiments. Error bars are SD.

Similarly the present inventors have tested efficacy of the combined therapy in patient derived ER+ breast tumour cells and found that p38 and MK2 inhibitors increased SMAC mimetic Compound A efficacy (FIG. 6)

Example 4: Co-Administration of SMAC Mimetics and p38 Inhibitors is Tolerable in Human and Mice The present inventors found that p38 inhibitors sensitised murine AML cells to Birinapant killing in vitro. However a critical test of the utility of the combination treatment is to determine whether is it a tolerable combination. Therefore preclinical studies in human cells and whole animals were performed to assess biosafety of the combination Birinapant and p38 inhibitors.

Figure 7:
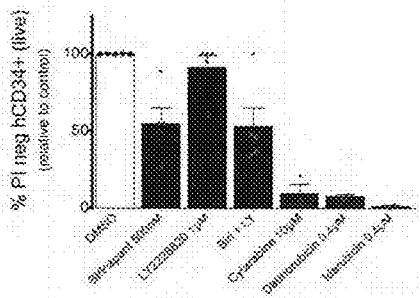
FIG. 7: Mice tolerate administration of birinapant plus p38 inhibitor. A. Mononuclear cells isolated from healthy donor by Ficoll sedimentation were treated for 48 h with indicated drugs. CD34$^+$ cell death was measured by staining with PI and flow cytometry. For each donor sample, graphs show mean of at least n=2 technical replicates across n=2-5 independent experiments. B and C. C57BL/6 mice were intra-peritoneally injected with vehicle (captisol 6%) or birinapant (B) or GT13072 (C) or LY2228820 or combination of LY2228820 and SM at indicated concentration. Mice received 8 injections twice a week over 4 weeks. Mice were euthanised 2 weeks after the treatment stopped. Graphs show organs, body weights and blood cell populations with 6 mice/group (B), 4 mice/group (C). Error bars are SEM.
Figure 7:
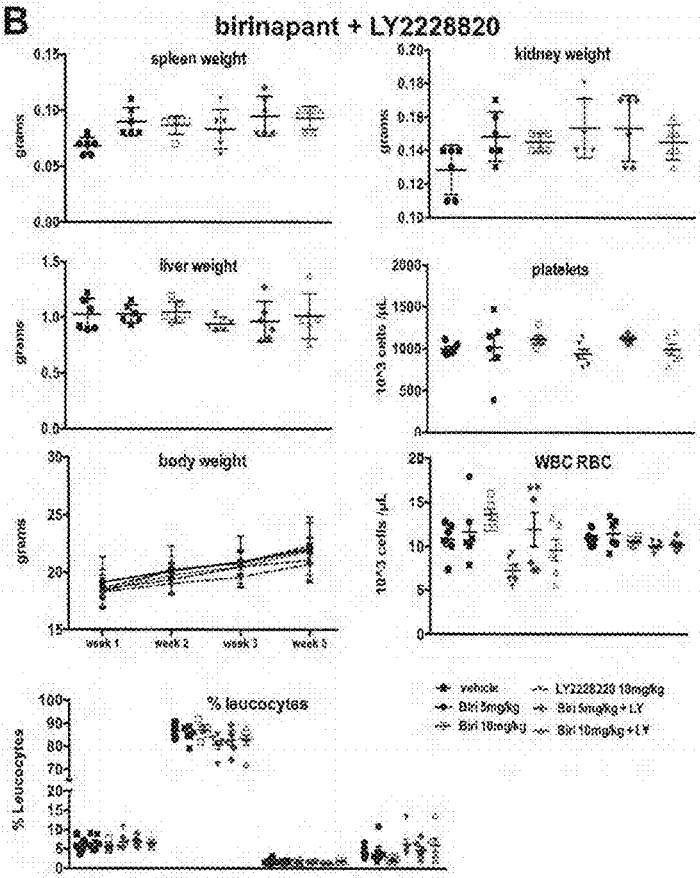
Figure 7:
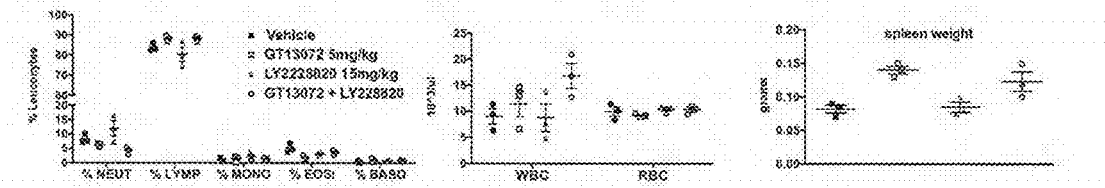

Birinapant combined with LY2228820 was far less toxic to normal CD34+ cells than conventional AML therapies: cytarabine, daunorubicin and idarubicin (FIG. 7A). This result indicates that the combination of birinapant and p38i is likely to be tolerated in human.

Because the safety of the combination treatment has not been reported in animals, the inventors evaluated the tolerability of the combination of smac-mimetic+p38 inhibitor in non tumour-bearing mice. After 4 weeks of co-administration of LY2228820 and two different doses of birinapant no overt acute or chronic toxicity was observed as determined by organ weights, body weight or blood cell populations (FIG. 7B). Most encouragingly, from a toxicity standpoint, administration of LY2228820 did not even exacerbate the splenomegaly induced by the more inflammatory smac-mimetic GT13072, nor affect the populations of white blood cells as determined by ADVIA analysis (FIG. 7C). These results indicate that the combination of SM and p38i is well tolerated in animals.

Figure 8:
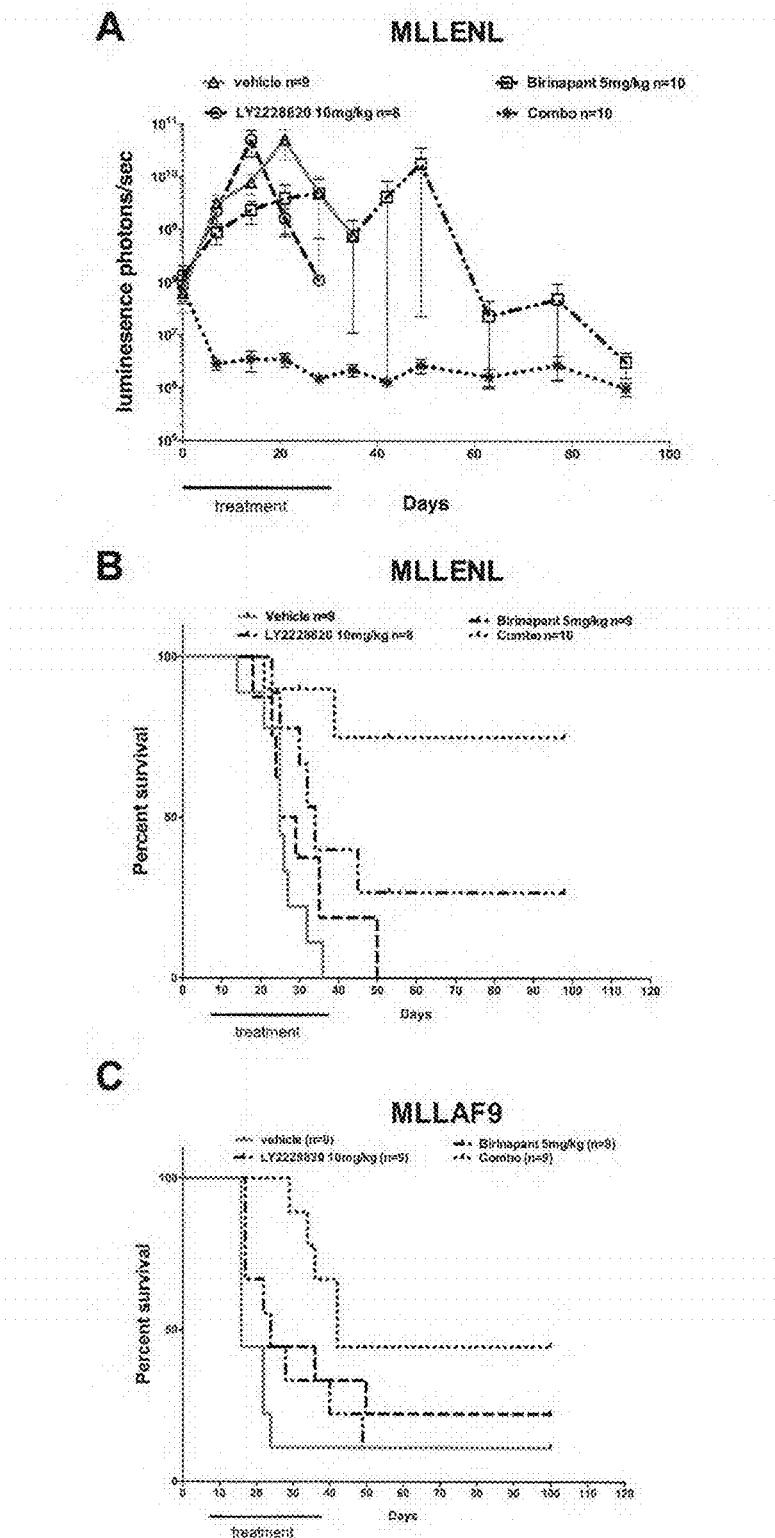
FIG. 8: Combination of birinapant with p38 inhibitor decreases AML tumor burden. Mice bearing MLLENL-luciferase (A and B) or MLL-AF9 (C) leukemic cells received i.p injections of birinapant (5 mg/kg), LY2228820 (10 mg/kg) or the combined drugs twice a week for 4 weeks. A. Representative data of in vivo imaging of leukaemia progression in mice bearing MLL-ENL-luciferase. B. Kaplan-Meier survival curve of mice bearing MLL-ENL-luciferase and treated or not with birinapant, LY222820 or combined therapy. C. Kaplan-Meier survival curve of mice bearing MLL-AF9 and treated or not with birinapant, LY222820 or combined therapy.

Example 5: Co-Administration of SMAC Mimetics and p38 Inhibitors in Mice Bearing Tumour To assess the therapeutic efficacy of the combination multiple primary MLL-ENL and MLL-AF9 leukemias were transplanted and the secondary recipient mice were treated with the different drugs. Congenic albino mice were injected with MLL-ENL cells co-expressing a luciferase gene. The engraftment and trafficking were evaluated by in vivo bioluminescent imaging. Treatment started when the photon emission average of the cohorts was one log above the background level, typically about 8 days after injection of leukemic cells (FIGS. 8A & B). Remarkably after only one week of treatment mice bearing MLLENL-Luc responded to the combined therapy, while vehicle, Birinapant alone or p38 inhibitor alone treated mice did not. Thus, by day 7 after initiating the treatment luciferase activity signals decreased only in mice that received the co-therapy (FIG. 8A). A significant decrease in leukemic burden with improved overall survival was observed in mice treated with the co-therapy compared to mice treated with monotherapy (FIG. 8B). The inventors tested an additional AML models of leukemia. In line with the MLL-ENL results, co-therapy considerably improved the survival of mice bearing MLL-AF9 AMLs compared to mice that received the single agents or no treatment (FIG. 8C).

CONCLUSION

SMAC mimetics are currently being evaluated in clinical trial for cancer treatment. Despite encouraging preclinical studies it is unlikely that SMAC mimetics will be efficient as a single agents to most of cancers. Therefore it is essential to better understand how SMAC mimetics kill cancer cells to improve their use in cancer therapy. A kinase inhibitors screen has revealed that inhibition of the p38/MK2 pathway increased TNFα secretion and subsequent death induced by SMAC mimetic. The present inventors have shown that p38 inhibitors and MK2 inhibitors efficiently sensitized AML, multiple myeloma and breast cancer to SMAC mimetics. Most importantly, it was demonstrated that the use of clinical p38 inhibitors and SMAC mimetic is well tolerated in mice. All together these results suggest that the cooperation between SMAC mimetics and p38 inhibitors or MK2 inhibitors, or both a p38 inhibitor and a MK2 inhibitor is likely to be a new therapeutic strategy to treat cancer.

REFERENCES

Almeida, R., and Allshire, R. C. (2005). RNA silencing and genome regulation. Trends in cell biology 15, 251-258.
Bertrand, M. J. M., Milutinovic, S., Dickson, K. M., Ho, W. C., Boudreault, A., Durkin, J., Gillard, J. W., Jaquith, J. B., Morris, S. J., and Barker, P. A. (2008). cIAP1 and cIAP2 facilitate cancer cell survival by functioning as E3 ligases that promote RIP1 ubiquitination. In Mol Cell, pp. 689-700.
Breaker, R. R., and Joyce, G. F. (1995). A DNA enzyme with Mg(2+)-dependent RNA phosphoesterase activity. Chem Biol 2, 655-660.
Carter, B. Z., Mak, D. H., Morris, S. J., Borthakur, G., Estey, E., Byrd, A. L., Konopleva, M., Kantarjian, H., and Andreeff, M. (2011). XIAP antisense oligonucleotide (AEG35156) achieves target knockdown and induces apoptosis preferentially in CD34+38− cells in a phase 1/2 study of patients with relapsed/refractory AML. Apoptosis: an international journal on programmed cell death 16, 67-74.
Cohen, P., and Alessi, D. R. (2013). Kinase Drug Discovery—What's Next in the Field? In ACS Chem Biol, pp. 96-104.
Du, C., Fang, M., Li, Y., Li, L., and Wang, X. (2000). Smac, a mitochondrial protein that promotes cytochrome c-dependent caspase activation by eliminating IAP inhibition. Cell 102, 33-42.
Duan, W., Chan, J. H., McKay, K., Crosby, J. R., Choo, H. H., Leung, B. P., Karras, J. G., and Wong, W. S. (2005). Inhaled p38alpha mitogen-activated protein kinase antisense oligonucleotide attenuates asthma in mice. American journal of respiratory and critical care medicine 171, 571-578.
Dueber, E. C., Schoeffler, A. J., Lingel, A., Elliott, J. M., Fedorova, A. V., Giannetti, A. M., Zobel, K., Maurer, B., Varfolomeev, E., Wu, P., et al. (2011). Antagonists induce a conformational change in cIAP1 that promotes autoubiquitination. In Science, pp. 376-380.
Eckelman, B. P., and Salvesen, G. S. (2006). The human anti-apoptotic proteins cIAP1 and cIAP2 bind but do not inhibit caspases. The Journal of biological chemistry 281, 3254-3260.
Feltham, R., Bettjeman, B., Budhidarmo, R., Mace, P. D., Shirley, S., Condon, S. M., Chunduru, S. K., McKinlay, M. A., Vaux, D. L., Silke, J., and Day, C. L. (2011). Smac mimetics activate the E3 ligase activity of cIAP1 protein by promoting RING domain dimerization. The Journal of biological chemistry 286, 17015-17028.
Feltham, R., Moulin, M., Vince, J. E., Mace, P. D., Wong, W. W., Anderton, H., Day, C. L., Vaux, D. L., and Silke, J. (2010). Tumor necrosis factor (TNF) signaling, but not TWEAK (TNF-like weak inducer of apoptosis)-triggered cIAP1 (cellular inhibitor of apoptosis protein 1) degradation, requires cIAP1 RING dimerization and E2 binding. The Journal of biological chemistry 285, 17525-17536.
Feoktistova, M., Geserick, P., Kellert, B., Dimitrova, D. P., Langlais, C., Hupe, M., Cain, K., MacFarlane, M., Hacker, G., and Leverkus, M. (2011). cIAPs block Ripoptosome formation, a RIP1/caspase-8 containing intracellular cell death complex differentially regulated by cFLIP isoforms. Molecular cell 43, 449-463.
Fulda, S. (2014). Inhibitor of Apoptosis (IAP) proteins in hematological malignancies: molecular mechanisms and therapeutic opportunities. Leukemia: official journal of the Leukemia Society of America, Leukemia Research Fund, UK 28, 1414-1422.
Fulda, S., and Vucic, D. (2012). Targeting IAP proteins for therapeutic intervention in cancer. In Nat Rev Drug Discov, pp. 109-124.
Gaestel, M. (2013). What goes up must come down: molecular basis of MAPKAP kinase 2/3-dependent regulation of the inflammatory response and its inhibition. Biological chemistry 394, 1301-1315.
Hess, C. J., Berkhof, J., Denkers, F., Ossenkoppele, G. J., Schouten, J. P., Oudejans, J. J., Waisfisz, Q., and Schuurhuis, G. J. (2007). Activated intrinsic apoptosis pathway is a key related prognostic parameter in acute myeloid leukemia. Journal of clinical oncology: official journal of the American Society of Clinical Oncology 25, 1209-1215.

Hiscott, J., Nguyen, T. L., Arguello, M., Nakhaei, P., and Paz, S. (2006). Manipulation of the nuclear factor-kappaB pathway and the innate immune response by viruses. Oncogene 25, 6844-6867.

Ishitsuka, K., Hideshima, T., Neri, P., Vallet, S., Shiraishi, N., Okawa, Y., Shen, Z., Raje, N., Kiziltepe, T., Ocio, E. M., et al. (2008). p38 mitogen-activated protein kinase inhibitor LY2228820 enhances bortezomib-induced cytotoxicity and inhibits osteoclastogenesis in multiple myeloma; therapeutic implications. British journal of haematology 141, 598-606.

Janssen, H. L., Reesink, H. W., Lawitz, E. J., Zeuzem, S., Rodriguez-Tones, M., Patel, K., van der Meer, A. J., Patick, A. K., Chen, A., Zhou, Y., et al. (2013). Treatment of HCV infection by targeting microRNA. The New England journal of medicine 368, 1685-1694.

Khachigian, L. M. (2002). DNAzymes: cutting a path to a new class of therapeutics. Current opinion in molecular therapeutics 4, 119-121.

McEleny, K., Coffey, R., Morrissey, C., Williamson, K., Zangemeister-Wittke, U., Fitzpatrick, J. M., and Watson, R. W. (2004). An antisense oligonucleotide to cIAP-1 sensitizes prostate cancer cells to fas and TNFalpha mediated apoptosis. The Prostate 59, 419-425.

Millar, A. A., and Waterhouse, P. M. (2005). Plant and animal microRNAs: similarities and differences. Functional & integrative genomics 5, 129-135.

Nakagawa, Y., Abe, S., Kurata, M., Hasegawa, M., Yamamoto, K., Inoue, M., Takemura, T., Suzuki, K., and Kitagawa, M. (2006). IAP family protein expression correlates with poor outcome of multiple myeloma patients in association with chemotherapy-induced overexpression of multidrug resistance genes. American journal of hematology 81, 824-831.

Navas, T. A., Nguyen, A. N., Hideshima, T., Reddy, M., Ma, J. Y., Haghnazari, E., Henson, M., Stebbins, E. G., Kerr, I., O'Young, G., et al. (2006) Inhibition of p38alpha MAPK enhances proteasome inhibitor-induced apoptosis of myeloma cells by modulating Hsp27, Bcl-X(L), Mcl-1 and p53 levels in vitro and inhibits tumor growth in vivo. Leukemia: official journal of the Leukemia Society of America, Leukemia Research Fund, UK 20, 1017-1027.

Pan, Q., Huang, Y., Chen, L., Gu, J., and Zhou, X. (2014). SMAC-armed vaccinia virus induces both apoptosis and necroptosis and synergizes the efficiency of vinblastine in HCC. Human cell.

Pasquinelli, A. E., Hunter, S., and Bracht, J. (2005). MicroRNAs: a developing story. Current opinion in genetics & development 15, 200-205.

Rahman, M. M., and McFadden, G. (2011). Modulation of NF-kappaB signalling by microbial pathogens. Nature reviews Microbiology 9, 291-306.

Ramp, U., Krieg, T., Caliskan, E., Mahotka, C., Ebert, T., Willers, R., Gabbert, H. E., and Gerharz, C. D. (2004). XIAP expression is an independent prognostic marker in clear-cell renal carcinomas. Human pathology 35, 1022-1028.

Santoro, S. W., and Joyce, G. F. (1997). A general purpose RNA-cleaving DNA enzyme. Proceedings of the National Academy of Sciences of the United States of America 94, 4262-4266.

Shukla, R., Yue, J., Siouda, M., Gheit, T., Hantz, O., Merle, P., Zoulim, F., Krutovskikh, V., Tommasino, M., and Sylla, B. S. (2011). Proinflammatory cytokine TNF-alpha increases the stability of hepatitis B virus X protein through NF-kappaB signaling. Carcinogenesis 32, 978-985.

Smith, N. A., Singh, S. P., Wang, M. B., Stoutjesdijk, P. A., Green, A. G., and Waterhouse, P. M. (2000). Total silencing by intron-spliced hairpin RNAs. Nature 407, 319-320.

Sokol, L., Cripe, L., Kantarjian, H., Sekeres, M. A., Parmar, S., Greenberg, P., Goldberg, S. L., Bhushan, V., Shammo, J., Hohl, R., et al. (2012). Randomized, dose-escalation study of the p38alpha MAPK inhibitor SCIO-469 in patients with myelodysplastic syndrome. Leukemia: official journal of the Leukemia Society of America, Leukemia Research Fund, UK.

Srinivasula, S. M., Hegde, R., Saleh, A., Datta, P., Shiozaki, E., Chai, J., Lee, R. A., Robbins, P. D., Fernandes-Alnemri, T., Shi, Y., and Alnemri, E. S. (2001). A conserved XIAP-interaction motif in caspase-9 and Smac/DIABLO regulates caspase activity and apoptosis. Nature 410, 112-116.

Tamm, I., Kornblau, S. M., Segall, H., Krajewski, S., Welsh, K., Kitada, S., Scudiero, D. A., Tudor, G., Qui, Y. H., Monks, A., et al. (2000). Expression and prognostic significance of IAP-family genes in human cancers and myeloid leukemias. Clinical cancer research: an official journal of the American Association for Cancer Research 6, 1796-1803.

Tamm, I., Richter, S., Oltersdorf, D., Creutzig, U., Harbott, J., Scholz, F., Karawajew, L., Ludwig, W. D., and Wuchter, C. (2004). High expression levels of x-linked inhibitor of apoptosis protein and survivin correlate with poor overall survival in childhood de novo acute myeloid leukemia. Clinical cancer research: an official journal of the American Association for Cancer Research 10, 3737-3744.

van der Oost, J., Westra, E. R., Jackson, R. N., and Wiedenheft, B. (2014). Unravelling the structural and mechanistic basis of CRISPR-Cas systems. Nature reviews Microbiology 12, 479-492.

Verhagen, A. M., Ekert, P. G., Pakusch, M., Silke, J., Connolly, L. M., Reid, G. E., Moritz, R. L., Simpson, R. J., and Vaux, D. L. (2000). Identification of DIABLO, a mammalian protein that promotes apoptosis by binding to and antagonizing IAP proteins. Cell 102, 43-53.

Vince, J. E., Wong, W. W.-L., Khan, N., Feltham, R., Chau, D., Ahmed, A. U., Benetatos, C. A., Chunduru, S. K., Condon, S. M., McKinlay, M., et al. (2007). IAP antagonists target cIAP1 to induce TNFalpha-dependent apoptosis. In Cell, pp. 682-693.

Waterhouse, P. M., Graham, M. W., and Wang, M. B. (1998). Virus resistance and gene silencing in plants can be induced by simultaneous expression of sense and antisense RNA. Proceedings of the National Academy of Sciences of the United States of America 95, 13959-13964.

Wooddell, C. I., Rozema, D. B., Hossbach, M., John, M., Hamilton, H. L., Chu, Q., Hegge, J. O., Klein, J. J., Wakefield, D. H., Oropeza, C. E., et al. (2013). Hepatocyte-targeted RNAi therapeutics for the treatment of chronic hepatitis B virus infection. Molecular therapy: the journal of the American Society of Gene Therapy 21, 973-985.

Yamamoto, K., Abe, S., Nakagawa, Y., Suzuki, K., Hasegawa, M., Inoue, M., Kurata, M., Hirokawa, K., and Kitagawa, M. (2004). Expression of IAP family proteins in myelodysplastic syndromes transforming to overt leukemia. Leukemia research 28, 1203-1211.

Zarnegar, B. J., Wang, Y., Mahoney, D. J., Dempsey, P. W., Cheung, H. H., He, J., Shiba, T., Yang, X., Yeh, W. C., Mak, T. W., et al. (2008). Noncanonical NF-kappaB activation requires coordinated assembly of a regulatory complex of the adaptors cIAP1, cIAP2, TRAF2 and TRAF3 and the kinase NIK. Nature immunology 9, 1371-1378.

Zuber, J., Radtke, I., Pardee, T. S., Zhao, Z., Rappaport, A. R., Luo, W., McCurrach, M. E., Yang, M. M., Dolan, M. E., Kogan, S. C., et al. (2009). Mouse models of human AML accurately predict chemotherapy response. Genes & development 23, 877-889.

The invention claimed is:

1. A method of treating cancer in a subject, the method comprising administering to the subject an IAP antagonist and a p38 inhibitor or a MK2 inhibitor, or both a p38 inhibitor and a MK2 inhibitor.

2. The method as claimed in claim 1 wherein the IAP antagonist is administered with a p38 antagonist or a MK2 inhibitor.

3. The method as claimed in claim 1 wherein the IAP is one or more of cIAP1, cIAP2 and XIAP.

4. The method as claimed in claim 1 wherein the antagonist is a SMAC mimetic.

5. The method as claimed in claim 4, wherein the SMAC mimetic comprises one or more of the following characteristics:
   (a) the SMAC mimetic is bivalent;
   (b) the SMAC mimetic derepresses XIAP-mediated caspase-3 repression;
   (c) the SMAC mimetic degrades cIAP-1 not bound to TRAF2 as well as cIAP1 bound to TRAF2;
   (d) the SMAC mimetic degrades cIAP-2 bound to TRAF2 but does not degrade cIAP-2 not bound to TRAF2;
   (e) the SMAC mimetic weakly degrades cIAP-2 not bound to TRAF2 relative to degradation of cIAP-2 bound to TRAF; and
   (f) the SMAC mimetic has the general structure [P1-P2-P3-P4] or [P1-P2-P3-P4]-L-[P1'-P2'-P3'-P4'], wherein P1-P2-P3- and P1'-P2'-P3'- correspond to peptide replacements or peptidomimetics of the N-terminal Ala-Val-Pro- tripeptide of mature SMAC and P4 and P4' correspond to amino acid replacements of Phe, Tyr, Ile, or Val, and L is a linking group, or bond, covalently linking [P1-P2-P3-P4] to [P1'-P2'-P3'-P4'].

6. The method as claimed in claim 4 wherein the SMAC mimetic is birinapant, GT13072 or GT12911.

7. The method as claimed in claim 1 wherein the antagonist reduces expression of the IAP gene.

8. The method as claimed in claim 7 wherein the IAP gene is the cIAP1, cIAP2 or XIAP gene.

9. The method as claimed in claim 7 wherein the antagonist is siRNA, shRNA or miRNA.

10. The method as claimed in claim 9 wherein the siRNA, shRNA or miRNA is targeted against a sequence selected from the group consisting of NCBI Reference Sequence: NM_001166.4, NCBI Reference Sequence: NM_001256163.1, NCBI Reference Sequence: NM_001256166.1, GenBank: DQ068066.1, NCBI Reference Sequence: NM_001165.4, NCBI Reference Sequence: NM_182962.2, GenBank: BC037420.1, NCBI Reference Sequence: NM_001167.3, NCBI Reference Sequence: NM_001204401.1, NCBI Reference Sequence: NR_037916.1, NCBI Reference Sequence: NG_007264.1, NCBI reference sequence NM_001167.3, NCBI reference sequence NM_001204401.1 and NCBI reference sequence NR_037916.1.

11. The method as claimed in claim 1 wherein the IAP antagonist is administered in combination with a p38 inhibitor.

12. The method as claimed in claim 11 wherein the p38 inhibitor is selected from the group consisting of LY2228820, SCIO-469, BIRB 796, VX-702, SB 239063, SB202190, BMS 582949, SB203580, GW856553X, Skepinone-L, PH-797804, VX-745, TAK-715, JX-401, CAY10571, SB220025, AMG 548, ML 3403, SKF 86002, SX 011, SB-681323, SB 242235, CMPD-1, DBM 1285 dihydrochloride, EO 1428 and RWJ 67657.

13. The method as claimed in claim 11 wherein the p38 inhibitor reduces expression of the p38 gene.

14. The method as claimed in claim 13 wherein the p38 inhibitor is siRNA, shRNA or miRNA.

15. The method as claimed in claim 14 wherein the siRNA, shRNA or miRNA is targeted against the sequence of p38α (MAPK14) Accession NM_001315 or p38β (MAPK11) Accession NM_002751.

16. The method as claimed in claim 1 wherein the IAP antagonist is administered in combination with a MK2 inhibitor.

17. The method as claimed in claim 16 wherein the MK2 inhibitor is selected from the group consisting of PF-3644022, PHA 767491, MK-2 Inhibitor III and MK-2 Inhibitor IV.

18. The method as claimed in claim 16 wherein the MK2 inhibitor reduces expression of the MK2 gene.

19. The method as claimed in claim 18 wherein the MK2 inhibitor is siRNA, shRNA or miRNA.

20. The method as claimed in claim 19 wherein the siRNA, shRNA or miRNA is targeted against the sequence of MK2 (MAPKAPK2) Accession NM_004759.

21. The method as claimed in claim 1 wherein the method comprises administering a polynucleotide encoding the IAP antagonist.

22. The method as claimed in claim 1 wherein the cancer is selected from AML, myelodysplastic syndrome, multiple myeloma, ALL, breast cancer, colorectal cancer and ovarian cancer.

23. A method of treating cancer, comprising:
   administering to a subject:
   an IAP antagonist;
   a p38 inhibitor; and
   a MK2 inhibitor.

24. The method as claimed in claim 23, wherein the IAP antagonist is selected from the group consisting of cIAP1, cIAP2 and XIAP.

25. The method as claimed in claim 24, wherein the IAP antagonist is a SMAC mimetic comprising a characteristic selected from the group consisting of:
   (a) the SMAC mimetic is bivalent;
   (b) the SMAC mimetic derepresses XIAP-mediated caspase-3 repression;
   (c) the SMAC mimetic degrades cIAP-1 not bound to TRAF2 as well as cIAP1 bound to TRAF2;
   (d) the SMAC mimetic degrades cIAP-2 bound to TRAF2 but does not degrade cIAP-2 not bound to TRAF2;
   (e) the SMAC mimetic weakly degrades cIAP-2 not bound to TRAF2 relative to degradation of cIAP-2 bound to TRAF; and
   (f) the SMAC mimetic has the general structure [P1-P2-P3-P4] or [P1-P2-P3-P4]-L-[P1'-P2'-P3'-P4'], wherein P1-P2-P3- and P1'-P2'-P3'- correspond to peptide replacements or peptidomimetics of the N-terminal Ala-Val-Pro- tripeptide of mature SMAC and P4 and P4' correspond to amino acid replacements of Phe, Tyr, Ile, or Val, and L is a linking group, or bond, covalently linking [P1-P2-P3-P4] to [P1'-P2'-P3'-P4'].

26. The method as claimed in claim 25, wherein the SMAC mimetic is selected from the group consisting of birinapant, GT13072 and GT12911.

27. The method as claimed in claim 26, wherein the antagonist reduces expression of an IAP gene.

28. The method as claimed in claim 27, wherein the IAP gene is selected from the group consisting of cIAP1, cIAP2 and XIAP gene.

29. The method as claimed in claim 27, wherein the IAP antagonist is selected from the group consisting of siRNA, shRNA and miRNA.

30. The method as claimed in claim 29 wherein the antagonist is targeted against a sequence selected from the group consisting of NCBI Reference Sequence: NM_001166.4, NCBI Reference Sequence: NM_001256163.1, NCBI Reference Sequence: NM_001256166.1, GenBank: DQ068066.1, NCBI Reference Sequence: NM_001165.4, NCBI Reference Sequence: NM_182962.2, GenBank: BC037420.1, NCBI Reference Sequence: NM_001167.3, NCBI Reference Sequence: NM_001204401.1, NCBI Reference Sequence: NR_037916.1, NCBI Reference Sequence: NG_007264.1, NCBI reference sequence NM_001167.3, NCBI reference sequence NM_001204401.1 and NCBI reference sequence NR_037916.1.

31. The method as claimed in claim 23 wherein the p38 inhibitor is selected from the group consisting of LY2228820, SCIO-469, BIRB 796, VX-702, SB 239063, SB202190, BMS 582949, SB203580, GW856553X, Skepinone-L, PH-797804, VX-745, TAK-715, JX-401, CAY10571, SB220025, AMG 548, ML 3403, SKF 86002, SX 011, SB-681323, SB 242235, CMPD-1, DBM 1285 dihydrochloride, EO 1428 and RWJ 67657.

32. A method of treating cancer comprising:
administering to a subject:
an IAP antagonist which reduces expression of an IAP gene; and
a P38 inhibitor in a form of a nucleotide sequence selected from the group consisting of siRNA, shRNA and miRNA; or
an MK2 inhibitor comprising a nucleotide sequence selected from the group consisting of siRNA, shRNA and miRNA.

33. The method as claimed in claim 32, wherein the nucleotide sequence is targeted against sequence MK2 (MAPKAPK2) Accession NM_004759.

34. A method of claim 32, wherein:
the IAP antagonist is birinapant;
the P38 inhibitor is LY222820; and
the MK2 inhibitor is PF-3644022.

35. A method of treating cancer in a subject, comprising:
administering to the subject an IAP antagonist and a MK2 inhibitor selected from the group consisting of PF-3644022, PHA 767491, MK-2 Inhibitor III and MK-2 Inhibitor IV.

* * * * *